(12) United States Patent
Banju et al.

(10) Patent No.: US 9,980,632 B2
(45) Date of Patent: May 29, 2018

(54) ENDOSCOPE SYSTEM

(71) Applicant: OLYMPUS CORPORATION, Tokyo (JP)

(72) Inventors: Kazuo Banju, Tokyo (JP); Tetsuyuki Sakamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/214,593

(22) Filed: Jul. 20, 2016

(65) Prior Publication Data

US 2016/0324399 A1 Nov. 10, 2016

Related U.S. Application Data

(63) Continuation of application No. PCT/JP2015/066714, filed on Jun. 10, 2015.

(30) Foreign Application Priority Data

Jun. 11, 2014 (JP) .................................. 2014-120761

(51) Int. Cl.
*A61B 1/00* (2006.01)
*A61B 1/018* (2006.01)
(Continued)

(52) U.S. Cl.
CPC ........ *A61B 1/0051* (2013.01); *A61B 1/00006* (2013.01); *A61B 1/008* (2013.01);
(Continued)

(58) Field of Classification Search
CPC ............ A61B 1/00004; A61B 1/00006; A61B 1/00009; A61B 1/016; A61B 1/0051;
(Continued)

(56) References Cited

U.S. PATENT DOCUMENTS

2002/0062062 A1* 5/2002 Belson ................. A61B 1/0053
600/146
2006/0149130 A1 7/2006 Bob et al.
(Continued)

FOREIGN PATENT DOCUMENTS

| JP | H01-148232 A | 6/1989 |
|---|---|---|
| JP | H06-105797 A | 4/1994 |

(Continued)

OTHER PUBLICATIONS

International Search Report dated Jul. 21, 2015 issued in PCT/JP2015/066714.

(Continued)

*Primary Examiner* — Anhtuan T Nguyen
*Assistant Examiner* — Aaron B Fairchild
(74) *Attorney, Agent, or Firm* — Scully, Scott, Murphy & Presser, P.C.

(57) ABSTRACT

An endoscope system of the present invention includes a control part has a computation part which computes the radius of curvature of the central axis of the instrument channel when the input signal is received and, may generate the first driving signal according to a result of the computation part computing the radius of curvature so that a treatment instrument at which a rigid part is provided to be easily inserted into a channel while a view of an observation part is limited from deviating from an object to be treated, even when a radius of curvature of a bending part is small while the bending part is bent.

6 Claims, 16 Drawing Sheets

(51) Int. Cl.
*A61B 1/05* (2006.01)
*A61B 5/06* (2006.01)
*H04N 5/225* (2006.01)
*A61B 1/005* (2006.01)
*G02B 23/24* (2006.01)
*A61B 1/008* (2006.01)
*A61B 1/01* (2006.01)
*A61B 1/06* (2006.01)

(52) U.S. Cl.
CPC .......... *A61B 1/0016* (2013.01); *A61B 1/0055* (2013.01); *A61B 1/0057* (2013.01); *A61B 1/00082* (2013.01); *A61B 1/00133* (2013.01); *A61B 1/00135* (2013.01); *A61B 1/00154* (2013.01); *A61B 1/01* (2013.01); *A61B 1/018* (2013.01); *A61B 1/05* (2013.01); *A61B 5/06* (2013.01); *G02B 23/24* (2013.01); *H04N 5/2256* (2013.01); *A61B 1/00009* (2013.01); *A61B 1/0052* (2013.01); *H04N 2005/2255* (2013.01)

(58) Field of Classification Search
CPC ... A61B 1/0052; A61B 1/0055; A61B 1/0056; A61B 1/0057
See application file for complete search history.

(56) References Cited

U.S. PATENT DOCUMENTS

2007/0078301 A1    4/2007  Kura et al.
2010/0022825 A1*   1/2010  Yoshie ............... A61B 1/00006
                                                        600/104

FOREIGN PATENT DOCUMENTS

JP      2006-122680 A     5/2006
JP      2007-089808 A     4/2007
WO      WO 2012/014532 A1 2/2012

OTHER PUBLICATIONS

Japanese Office Action dated Jan. 5, 2016 issued in JP 2015-556311.

* cited by examiner

ENDOSCOPE SYSTEM

CROSS REFERENCE TO RELATED APPLICATIONS

This application is a continuation application based on a PCT Patent Application No. PCT/JP2015/066714, filed Jun. 10, 2015, whose priority is claimed on Japanese Patent Application No. 2014-120761, filed on Jun. 11, 2014, the entire content of which are hereby incorporated by reference.

BACKGROUND OF THE INVENTION

Field of the Invention

The present invention relates to an endoscope system which observes an object to be treated.

Description of the Related Art

In recent years, an endoscope system has been used for observing and treating an object to be treated in a body cavity, or the like. As this type of the endoscope system, for example, a system described in PCT International Publication No. 2012/014532 WO is known.

The endoscope system disclosed in Patent Literature 1 includes an endoscope which images an object to be treated, a control unit which is detachably connected to the endoscope, and a monitor which is connected to the control unit to display the object to be treated which is imaged by the endoscope.

The endoscope has an elongated insertion part which has flexibility, and an operation part provided at a proximal end portion of the insertion part. From a distal side toward the proximal side, the insertion part has a rigid part, a bending part, and a flexible tube part.

At the rigid part, an imaging surface of an imaging unit (observation part) and a distal end opening part of a treatment instrument insertion channel (an instrument channel) are provided.

From the rigid part toward the flexible tube part, the bending part has a first bending part, a second bending part, and a third bending part. For example, the first bending part is bent vertically and horizontally. The second bending part is vertically bent, and the third bending part is horizontally bent.

At an operation part main body included in the operation part, a first bending operation part which operates the first bending part to be bent is provided. At the operation part main body, a second bending operation part which operates the second bending part to be bent is provided.

A first bending operation mechanism having, for example, a pulley, is connected to the first bending operation part, and a second bending operation mechanism having, for example, a pulley, is connected to the second bending operation part.

At the operation part main body, a third bending operation part which operates the third bending part to be bent, a driving part having a driving force for electrically bending the third bending part in a horizontal direction and provided at the operation part main body, and a third bending operation mechanism in the horizontal direction to which the driving force of the driving part is transmitted are provided. The driving part is, for example, a motor.

The control unit has a bending angle calculation part which calculates a bending angle of the first bending part to the third bending part and a control part which controls the driving part according to a calculation result calculated by the bending angle calculation part so that the distal end portion of the insertion part comes closer to a target point (an object to be treated) due to the bending of the third bending part.

When a control operation part included in the operation part main body is operated, the control part sets a point which is, for example, spaced a desired distance from the imaging surface of the imaging unit toward an inside of a body cavity as a target point. Here, the control part calculates a position of the target point.

In addition, when the third bending part is bent, the control part determines, according to the calculation result (bending angle) calculated by the bending angle calculation part, whether the target point is disposed within a captured image (imaged viewing angle) imaged by the imaging surface.

When the target point is disposed within the captured image, the control part controls the driving part according to the calculation result calculated by the bending angle calculation part so that the distal end portion of the insertion part comes closer to the target point due to the bending of the third bending part.

By controlling the target point to continuously be positioned within the captured image, the target point is continuously displayed on the monitor, and an operator may easily operate the endoscope system.

SUMMARY

According to a first aspect of the present invention, an endoscope system includes an insertion part having flexibility and an instrument channel into which a medical instrument is insertable formed therein, a flexible tube part provided at a proximal end portion of the insertion part, a bending part provided at a distal end portion of the insertion part and bendable with respect to a distal end portion of the flexible tube part, a tubular body in which an insertion part channel into which the flexible tube part is insertable is formed and provided to be movable along a longitudinal axis of the flexible tube part with respect to the flexible tube part, a first driving part configured to operate the bending part to be bent with respect to the distal end portion of the flexible tube part, a second driving part provided at a distal end portion of the tubular body to drive the flexible tube part inserted into the insertion part channel toward a proximal end portion with respect to the tubular body, and a control part configured to generate a first driving signal which drives the first driving part so that the bending part is operated to be bent in a direction in which a radius of curvature of a central axis of the instrument channel enlarges and a second driving signal which drives the second driving part according to a first driving signal which drives the first driving part, and configured to perform control for transmitting the first driving signal to the first driving part and transmitting the second driving signal to the second driving part.

According to a second aspect of the present invention, the endoscope system according to the first aspect may further include a position detection part provided at a connection part which connects the flexible tube part to the bending part to detect a position of a distal end rigid part of the medical instrument which moves within the instrument channel and to transmit a result of detecting the position of the distal end rigid part of the medical instrument as an input signal to the control part. The control part may have a computation part which computes the radius of curvature of the central axis of the instrument channel when the input signal is received and, may generate the first driving signal according to a result of the computation part computing the radius of curvature.

According to a third aspect of the present invention, in the first aspect, the second driving part may move the flexible tube part in the longitudinal direction with respect to the tubular body according to the second driving signal from the control part.

According to a fourth aspect of the present invention, the endoscope system according to the first aspect may further include an observation unit provided at a distal end of the bending part. In the first aspect, the control part generates the second driving signal so that the field of view of the observation unit after the bending part is operated to be bent according to the first driving signal includes a center of the field of view of the observation unit before the bending part is operated to be bent.

According to a fifth aspect of the present invention, an endoscope system includes a flexible tube part having an instrument channel into which a medical instrument is insertable formed therein, a bending part having flexibility and provided at a distal end portion of the flexible tube part and bendable, a driving part which operates the bending part to be bent with respect to the distal end portion of the flexible tube part, an expansion-and-contraction part which has a space between an inner circumferential surface and an outer circumferential surface of the flexible tube part, and which expands and contracts the flexible tube part in the direction of its longitudinal axis, a fluid control part which controls supply of the fluid to the space of the expansion-and-contraction part and suction of the fluid from the space, a control part which operates the bending part to be bent in a direction in which a radius of curvature of a central axis of the instrument channel enlarges and performs control for contracting the expansion-and-contraction part in the direction of its longitudinal axis by controlling the fluid control part so that the fluid in the space is suctioned.

According to a sixth aspect of the present invention, in the fifth aspect, the expansion-and-contraction part may be formed in a bellows.

DETAILED DESCRIPTION OF THE PREFERRED EMBODIMENTS

First Embodiment

Hereinafter, a first embodiment of an endoscope system related to the present invention will be described with reference to FIGS. 1 to 17.

Figure 1:
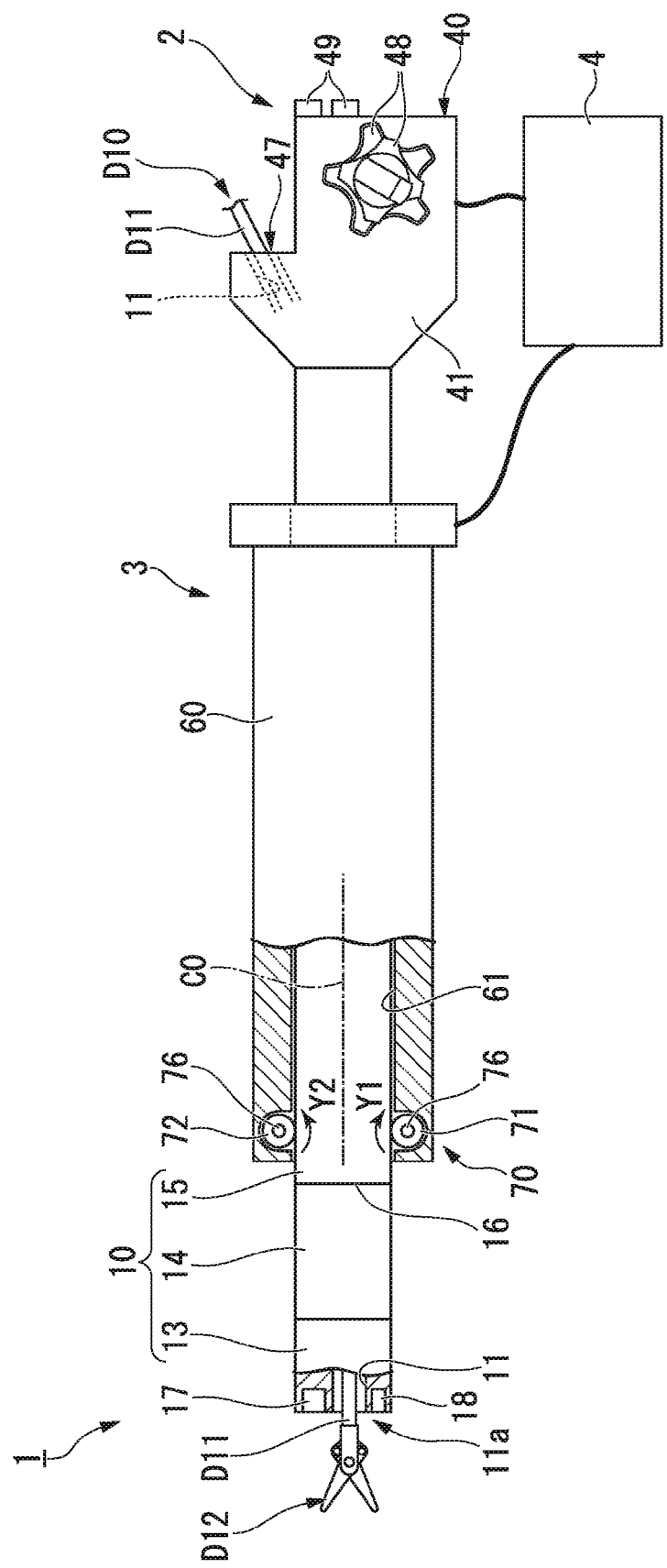
FIG. 1 is an overall view in which a part of an endoscope system according to a first embodiment of the present invention is cut.
Figure 2:
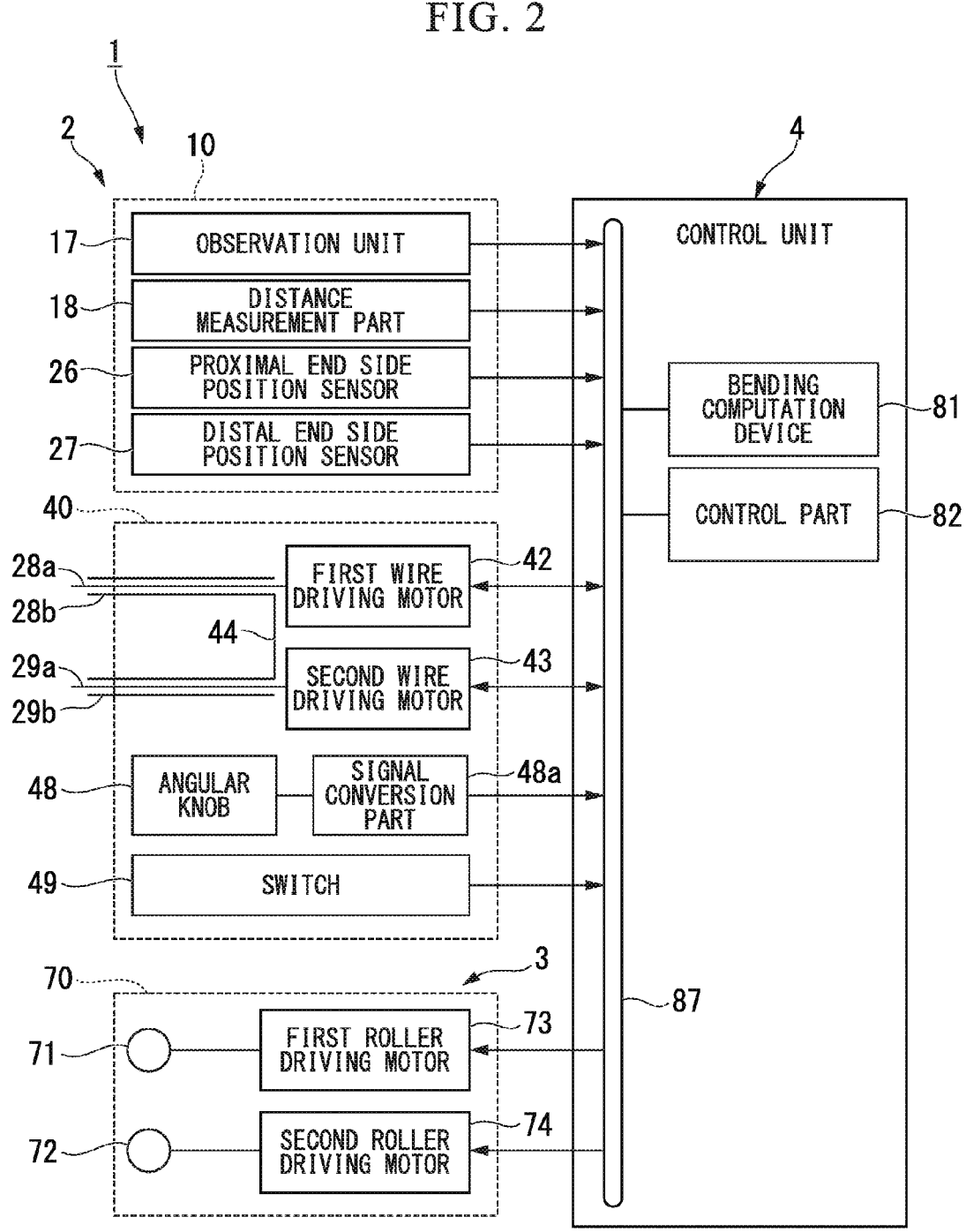
FIG. 2 is a block diagram of the endoscope system.

As shown in FIGS. 1 and 2, an endoscope system 1 according to the embodiment includes an endoscope apparatus 2 having an insertion part 10 which is flexible, an overtube (tubular body) 3 in which an insertion part channel 61 into which the insertion part 10 is insertable is formed, and a control unit 4 which controls the endoscope apparatus 2 and the overtube 3.

Figure 3:
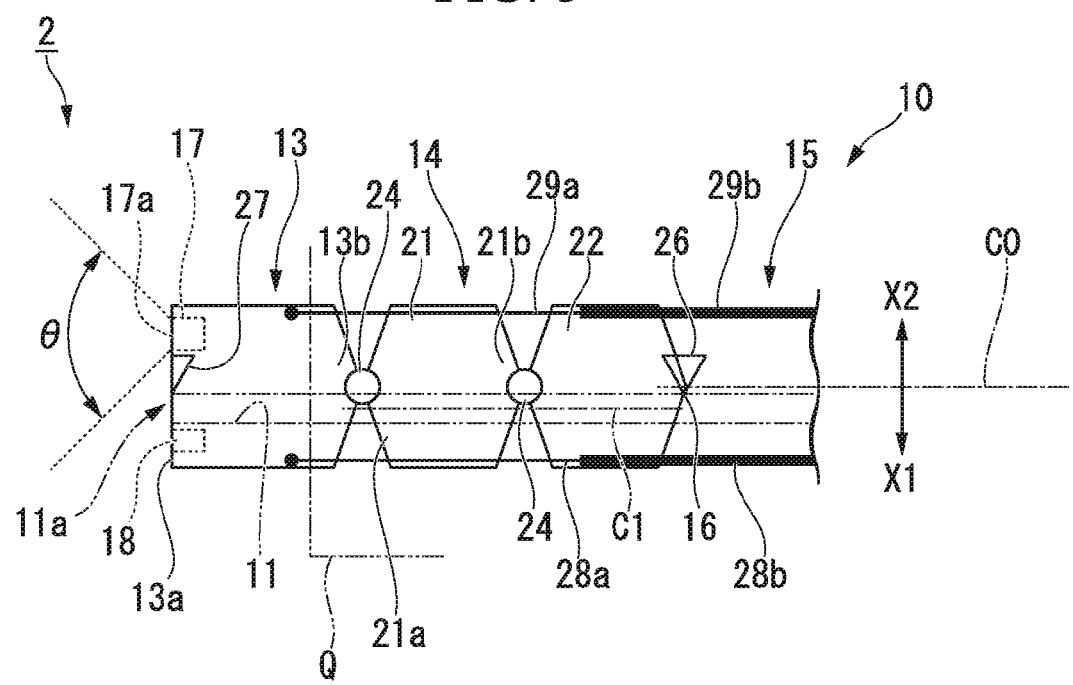
FIG. 3 is a lateral view of an insertion part in an endoscope apparatus of the endoscope system.

As shown in FIGS. 1 and 3, the endoscope apparatus 2 includes the insertion part 10 described above formed in a long shape and an operation part 40 provided at a proximal end portion of the insertion part 10. The endoscope apparatus 2 is a so-called straight view type in which the front of the insertion part 10 is observable.

Hereinafter, a direction toward the insertion part 10 with respect to the operation part 40 and a direction toward the operation part 40 with respect to the insertion part 10 to be described below will be referred to as a distal end side and a proximal end side, respectively.

All of the drawings are shown schematically and show only the elements that are important in describing the embodiment for convenience of description. In addition, ratios of thicknesses or size of the elements are adjusted for the drawings to be easily viewable.

First, a treatment instrument (medical instrument) used along with the endoscope system 1 will be described.

As shown in FIG. 1, in a treatment instrument D10 used by being inserted into a channel (instrument channel) 11 of the endoscope apparatus 2, a rigid distal end rigid part D12 is provided at a distal end portion of a flexible treatment instrument insertion part D11. In this embodiment, the treatment instrument D10 is a biopsy forceps.

Figure 18:
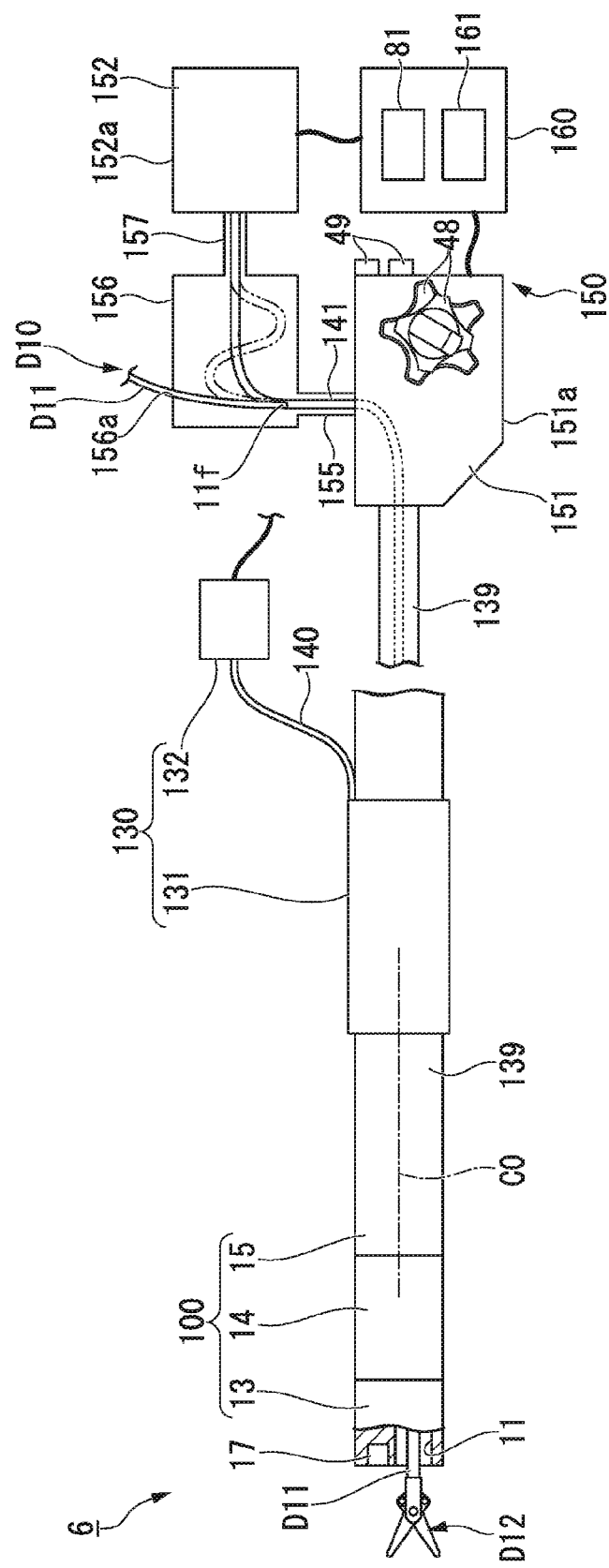
FIG. 18 is an overall view in which a part of an endoscope system according to a second embodiment of the present invention is cut.

In the drawings other than FIGS. 1 and 18, the distal end rigid part D12 is schematically shown.

As shown in FIGS. 1 and 3, the insertion part 10 has a rigid part 13 provided at a distal end portion, a bending part 14 disposed further toward the proximal end side than the rigid part 13 and capable of being operated to be bent, and a flexible tube part 15 disposed further toward the proximal end side than the bending part 14.

The rigid part 13 is formed with a rigid metal such as stainless steel in a cylindrical shape. For example, a distal end portion of a lighting unit having a light guide (not shown) and an observation unit (observation part) 17 having an imaging element such as a charge coupled device (CCD) are fixed to a distal end surface 13a of the rigid part 13 while exposed to the outside. The observation unit 17 acquires an image (image) within a viewing angle θ in front of the distal end surface 13a of the insertion part 10 which is focused on a light-receiving surface 17a of the imaging element, converts data representing the image into a signal, and transmits the signal to the control unit 4. The light receiving surface 17a of the observation unit 17 is provided further toward the distal end side than the bending part 14 of the insertion part 10.

As shown in FIG. 3, at the distal end surface 13a of the rigid part 13, an opening 11a of a distal end portion of the channel 11 is formed and the distal end of the channel 11 is fixed to the rigid part 13. The channel 11 is formed along an axis of the insertion part 10.

At a proximal end portion of the rigid part 13, a pair of proximal end side protruding parts 13b which protrude from positions spaced apart in a diameter direction of the rigid part 13 toward the proximal end side are provided (hereinafter, only one of the pair of proximal end side protruding parts 13b, a pin 24, and so on, will be shown.)

The bending part 14 is formed with a metal such as stainless steel in the shape of a tube and has two joint rings 21 and 22 arranged from the distal end side toward the proximal end side. Since the joint rings 21 and 22 are in the same shape, only the joint ring 21 will be described.

At a distal end portion of the joint ring 21, a pair of distal end side protruding parts 21a which protrude from positions spaced apart in a diameter direction of the joint ring 21 toward the distal end side are provided. At a proximal end portion of the joint ring 21, a pair of proximal end side protruding parts 21b which protrude from positions spaced apart in the diameter direction of the joint ring 21 toward the proximal end side are provided.

The proximal end side protruding part 13b at one side of the rigid part 13 and the distal end side protruding part 21a at one side of the joint ring 21 are connected via the pin 24, and the proximal end side protruding part 13b at the other side of the rigid part 13 and the distal end side protruding part 21a at the other side of the joint ring 21 are connected via the pin 24.

Likewise, the joint ring 21 and the joint ring 22 are also connected to each other by a pair of pins 24. An axis of the pin 24 which connects the rigid part 13 to the joint ring 21 and an axis of the pin 24 which connects the joint ring 21 to the joint ring 22 are parallel to each other.

With respect to the joint ring 22, the joint ring 21 may swivel on a virtual plane Q which is perpendicular to the axis of the pin 24. With respect to the joint ring 21, the rigid part 13 may swivel on the virtual plane Q which is perpendicular to the axis of the pin 24.

In addition, the number of the joint rings 21 and 22 included in the bending part 14 is not limited to two and may also be three or more.

The joint ring 22 is connected to the flexible tube part 15.

As shown in FIG. 3, at a position of a connection part 16 which connects the bending part 14 to the flexible tube part 15 in the channel 11, a proximal end side position sensor (position detection part) 26 is provided. At a position of the opening 11a in the channel 11, a distal end side position sensor 27 is provided.

Since configurations of the proximal end side position sensor 26 and the distal end side position sensor 27 are the same, the proximal end side position sensor 26 will be described as an example.

Figure 4:
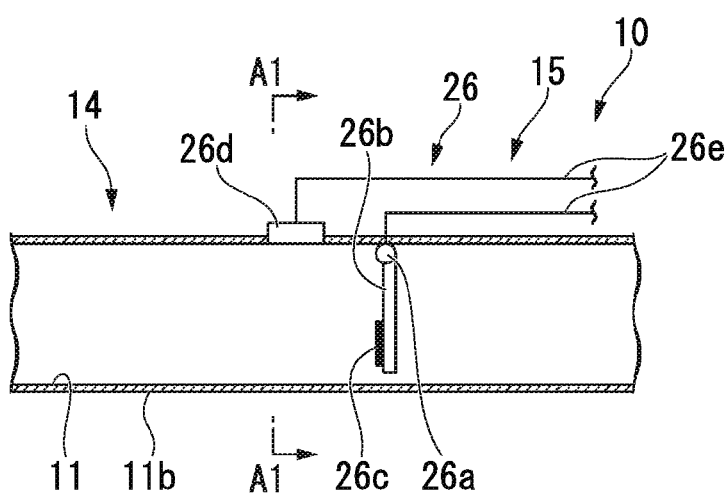
FIG. 4 is a cross-sectional view a lateral surface showing a position sensor provided at the insertion part.
Figure 5:
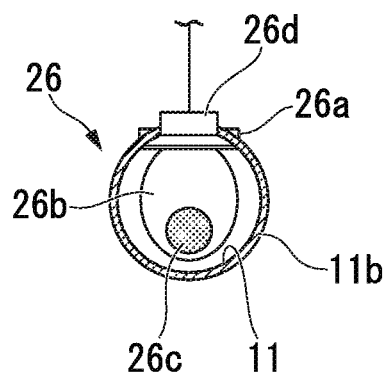
FIG. 5 is a cross-sectional view taken along section line A1-A1 in FIG. 4.

As shown in FIGS. 4 and 5, the proximal end side position sensor 26 has, for example, a rotation shaft member 26a mounted on a tube 11b which forms the channel 11, a shutter 26b having one end portion supported to be rotatable about a circumference of the rotation shaft member 26a, a contact (contact surface) 26c mounted on a distal end side surface at the other end portion of the shutter 26b, and a contact (contact surface) 26d mounted within a duct of the tube 11b to be exposed.

When not in contact with the treatment instrument D10, the shutter 26b is disposed to block the channel 11 by being biased by a spring member (not shown), and so on. The contact 26d is disposed at a position which allows coming in contact with the contact 26c when the shutter 26b has rotated about the circumference of the rotation shaft member 26a.

End portions of wires 26e are connected to the contact 26c and the contact 26d, respectively.

In an initial state in which there is no contact with the treatment instrument D10, the pair of wires 26e are insulated from each other.

Figure 6:
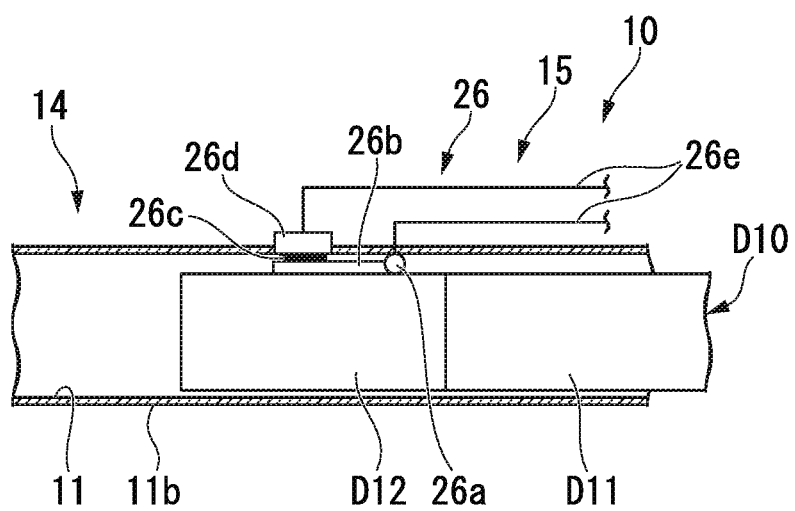
FIG. 6 is a cross-sectional view of a lateral surface which shows a state in which a rigid part of a treatment instrument is inserted into a part where the position sensor of a channel of the endoscope system is provided.

When the treatment instrument D10 is inserted from the proximal end side of the channel 11, and the treatment instrument D10 is moved toward the distal end side with respect to the channel 11 (when the treatment instrument D10 is pushed into the channel 11), as shown in FIG. 6, the distal end rigid part D12 resists an elastic force of the spring member, and the shutter 26b is pushed toward the distal end side. In this way, the shutter 26b rotates about the circumference of the rotation shaft member 26a. At a central line (longitudinal axis) C0 of the flexible tube part 15, when a distal end of the distal end rigid part D12 moves to a position which becomes a boundary between the bending part 14 and the flexible tube part 15, the contact 26c comes in contact with the contact 26d, and electricity is conducted between the pair of wires 26e.

In this way, a position of the distal end rigid part D12 provided at the treatment instrument D10 in the channel 11 when the contact 26c has come in contact with the contact 26d is detected. The proximal end side position sensor 26 converts the detected result into a signal and transmits the signal to the control unit 4. Even when the treatment instrument D10 is moved further forward in the channel 11, the state that which the contact 26c comes in contact with the contact 26d, and that electricity is conducted therebetween the pair of wires 26e is maintained.

As shown in FIG. 3, a distal end portion of a first operation wire 28a is connected to a first side X1 with respect to the central line C0 of the flexible tube part 15 at the proximal end side of the rigid part 13 by welding, and so on. The first operation wire 28a is inserted into the coil sheath 28b. A distal end portion of the coil sheath 28b is connected to the first side X1 with respect to the central line C0 at the joint ring 22 by welding and so on.

A distal end portion of the second operation wire 29a is connected to a second side X2 with respect to the central line C0 of the proximal end side of the rigid part 13 by welding, and so on. The second operation wire 29a is inserted into a coil sheath 29b. A distal end portion of the coil sheath 29b is connected to the second side X2 with respect to the central line C0 at the joint ring 22 by welding, and so on.

By moving (restoring) a first operation wire 28a toward the proximal end side with respect to a coil sheath 28b, the bending part 14 is bent to (toward) the first side X1 with respect to the central line C0. At this time, the second operation wire 29a is moved (pushed in) toward the distal end side with respect to the coil sheath 29b.

Here, a direction in which the bending part 14 is bent refers to a direction in which the distal end portion of the bending part 14 is deflected with respect to the central line C0 at the proximal end of the bending part 14.

Meanwhile, by restoring the second operation wire 29a, the bending part 14 is bent to the second side X2 with respect to the central line C0. At this time, the first operation wire 28a is pushed in.

In this way, by restoring the first operation wire 28a or the second operation wire 29a, the bending part 14 may be operated to be bent.

Whether the distal end rigid part D12 of the treatment instrument D10 can be inserted into the channel 11 formed in the bending part 14 is determined according to an outer diameter of the distal end rigid part D12 or a radius of curvature of central line C1 (refer to FIG. 3) of the channel 11 formed in the bending part 14. That is, when the outer diameter of the distal end rigid part D12 is similar to an inner diameter of the channel 11 formed in the bending part 14, due to the distal end rigid part D12 being stuck in an inner circumferential surface of the channel 11 formed in the bending part 14, it becomes difficult for the distal end rigid part D12 to be inserted into the channel 11.

In addition, when the bending part 14 is bent, since the channel 11 formed in the bending part 14 is also bent with a radius of curvature which is nearly the same as that of the bending part 14, a radius of curvature of the central line C1 of the channel 11 formed in the bending part 14 also decreases in accordance with a decrease of a radius of curvature of an axis of the bending part 14, and thus it is difficult to insert the distal end rigid part D12 into the channel 11 bent with the small radius of curvature.

Since the rigid part 13 is formed with a rigid material, even when the bending part 14 is operated to be bent, a distance between the distal end of the bending part 14 and the light-receiving surface 17a of the observation unit 17 and a direction of the light-receiving surface 17a of the observation unit 17 with respect to the distal end of the bending part 14 remain the same.

The bending part 14 may be freely bent on the virtual plane Q with respect to the distal end surface of the flexible tube part 15.

As shown in FIGS. 1 and 2, the operation part 40 has an operation part main body 41, a first wire driving motor (first driving part, driving part) 42 and a second wire driving motor (first driving part) 43 provided in the operation part main body 41, and a support member 44.

The wire driving motors 42 and 43 and the support member 44 are fixed to the operation part main body 41.

The proximal end portion of the first operation wire 28a is connected to a rotation shaft (not shown) of the first wire driving motor 42. The proximal end portion of the coil sheath 28b into which the first operation wire 28a is inserted is fixed to the support member 44.

Likewise, the proximal end portion of the second operation wire 29a is connected to a rotation shaft (not shown) of the second wire driving motor 43. The proximal end portion of the coil sheath 29b into which the second operation wire 29a is inserted is fixed to the support member 44.

By supplying power to the first wire driving motor 42 and rotating the rotation shaft of the first wire driving motor 42 toward the first side, the first operation wire 28a is restored with respect to the coil sheath 28b, and the bending part 14 is bent to the first side X1 with respect to the central line C0.

Meanwhile, by supplying power to the second wire driving motor 43 and rotating the rotation shaft of the second wire driving motor 43 toward the first side, the second operation wire 29a is restored with respect to the coil sheath 29b, and the bending part 14 is bent to the second side X2 with respect to the central line C0.

In this way, by restoring the operation wires 28a and 29a, the wire driving motors 42 and 43 of the operation part 40 may operate the bending part 14 to be bent with respect to the distal end portion of the flexible tube part 15.

A potentiometer (not shown) is embedded in the wire driving motors 42 and 43. A rotational amount from a reference position of the rotation shafts of the wire driving motors 42 and 43 is detected by the potentiometer. The potentiometer converts the detected result into a signal and transmits the signal to the control unit 4. In addition, the potentiometer may also be provided to be externally mounted with respect to the first wire driving motor 42 or the second wire driving motor 43.

In this embodiment, the bending part 14 is bent to the first side X1 and the second side X2 on the virtual plane Q with respect to the distal end surface of the flexible tube part 15. That is, the bending part 14 is bent in two directions with respect to the central line C0. In addition, the bending part 14 may also be configured to be bent in four directions at equiangular intervals along the circumference of the central line C0.

As shown in FIG. 1, a forceps hole 47 is provided at the operation part main body 41. The proximal end portion of the channel 11 is connected to the forceps hole 47. That is, the proximal end portion of the channel 11 is open further toward the proximal end side than the bending part 14.

An angular knob 48 which operates the wire driving motors 42 and 43 described above with a control part 82 to be described below is provided at the proximal end side of the operation part main body 41.

A signal conversion part 48a which converts a rotational amount of the angular knob 48 into a signal is connected to the angular knob 48 (refer to FIG. 2). As will be described below, the bending part 14 may be bent in a desired direction by operating the angular knob 48 when a control mode of the control part 82 is a manual operation mode.

At the operation part main body 41, a switch 49 which inputs a type of the treatment instrument D10 inserted into the channel 11 is provided.

As shown in FIGS. 1 and 2, the overtube 3 includes a tube main body 60 in which the insertion part channel 61 described above is formed and a movement mechanism 70 provided in the tube main body 60.

The tube main body 60 is formed with a material such as ethylene tetrafluoroethylene (ETFE) in the shape of a tube.

The movement mechanism 70 includes a pair of rollers 71 and 72 rotatably provided at a distal end portion of the tube main body 60, a first roller driving motor (second driving part) 73 which drives rotations of the rollers 71 and 72, and a second roller driving motor (second driving part) 74.

Since the roller 71 is supported by a rotation shaft member 76 in the tube main body 60, the roller 71 may rotate about a circumference of the rotation shaft member 76. The roller 72 is constituted in the same way as the roller 71.

Portions of the rollers 71 and 72 protrude from an inner circumferential surface of the insertion part channel 61. The distance between the roller 71 and the roller 72 is equal to an outer diameter of the insertion part 10 of the endoscope apparatus 2 or slightly shorter than the outer diameter of the insertion part 10 of the endoscope apparatus 2. The insertion part 10 inserted into the insertion part channel 61 is sandwiched between the rollers 71 and 72. Although not shown, the roller 71 is connected directly or via a reducer having a gear, for example, to a rotation shaft of the first roller driving motor 73. Likewise, the roller 72 is connected to a rotation shaft of the second roller driving motor 74.

By supplying power to the first roller driving motor 73 and rotating the rotation shaft of the first roller driving motor 73 toward the first side, the roller 71 may be rotated in a direction Y1 of the circumference of rotation shaft member 76. Likewise, by supplying power to the second roller driving motor 74 and rotating the rotation shaft of the second roller driving motor 74 toward the first side, the roller 72 may be rotated in a direction Y2 of the circumference of rotation shaft member 76.

By rotating the rollers 71 and 72 in this way, the movement mechanism 70 moves the observation unit 17 of the insertion part 10 inserted into the insertion part channel 61 toward the proximal end side with respect to the tube main body 60.

As shown in FIG. 2, the control unit 4 includes a bending computation device (computation part) 81 which performs computation according to a signal transmitted from the potentiometer of the wire driving motors 42 and 43 and the control part 82 which controls the wire driving motors 42 and 43, and so on, of the operation part 40.

Although not shown, the bending computation device 81 and the control part 82 are constituted with a computing element, a memory (memory part), a control program, and so on.

The bending computation device 81 and the control part 82 are connected to a bus 87.

The observation unit 17, a distance measurement part 18, the position sensors 26 and 27, the wire driving motors 42 and 43, the signal conversion part 48a, the switch 49, and the roller driving motors 73 and 74 are connected to the bus 87.

When the rotation shaft of the first wire driving motor 42 rotates from the reference position toward the first side, the first operation wire 28a is restored from a neutral position at which the bending part 14 is straight, and the bending part 14 is bent to the first side X1 with respect to the central line C0. In this way, the axis C1 of the bending part 14 is bent with a predetermined radius of curvature. In this manner, there is a predetermined correlation between an amount in which the operation wires 28a and 29a are restored from the neutral position of the bending part 14 and the radius of curvature of the central line C0 when the bending part 14 is bent.

In the memory of the bending computation device 81, a table (chart) which shows a correlation between rotational amounts of the rotation shafts of the wire driving motors 42 and 43 from the reference position and a radius of curvature of the axis C1 of the channel 11 formed in the bending part 14 when the bending part 14 is bent is stored. The computing element of the bending computation device 81 computes the radius of curvature of the axis C1 of the channel 11 according to the table stored in the memory from signals which represent the rotational amounts of the rotation shafts of the wire driving motors 42 and 43 transmitted from the potentiometer.

A bending amount of the bending part 14 is computed according to the rotational amounts of the rotation shafts of the wire driving motors 42 and 43 from the reference position.

In this way, the bending computation device 81 computes the radius of curvature of the central line C1 of the channel 11 formed in the bending part 14 when the bending part 14 is bent and the bending amount of the bending part 14.

The control part 82 includes the manual operation mode and an automatic operation mode as control modes. Immediately after the endoscope system 1 is started, the control mode is set to be the manual operation mode.

In the manual operation mode, the operator is capable of rotating the angular knob 48 from the neutral position to the first side by a predetermined angle.

When a position of a distal end of the distal end rigid part D12 of the treatment instrument D10 is detected by the proximal end side position sensor 26 as to be described below, the control mode of the control part 82 is automatically switched from the manual operation mode to the automatic operation mode.

In the automatic operation mode, the control part 82 automatically controls the wire driving motors 42 and 43 according to the position sensors 26 and 27 and the computation result of the bending computation device 81. When the control mode is the automatic operation mode, a clutch mechanism (not shown) is present so that the bending part 14 cannot be operated to be bent even when the operator operates the angular knob 48, or the angular knob 48 is locked to be unable to be operated.

In the automatic operation mode, the control part 82 automatically controls the wire driving motors 42 and 43 according to the radius of curvature of the central line C1 of the channel 11 formed in the bending part 14 and the bending amount of the bending part 14 computed by the bending computation device 81. The automatic operation mode will be described in detail later.

In the memory of the control part 82, for example, a table which represents a correlation between a type of the treatment instrument D10 and a predetermined value which represents the radius of curvature of the central line C1 of the channel 11 formed in the bending part 14 is stored.

Figure 7:
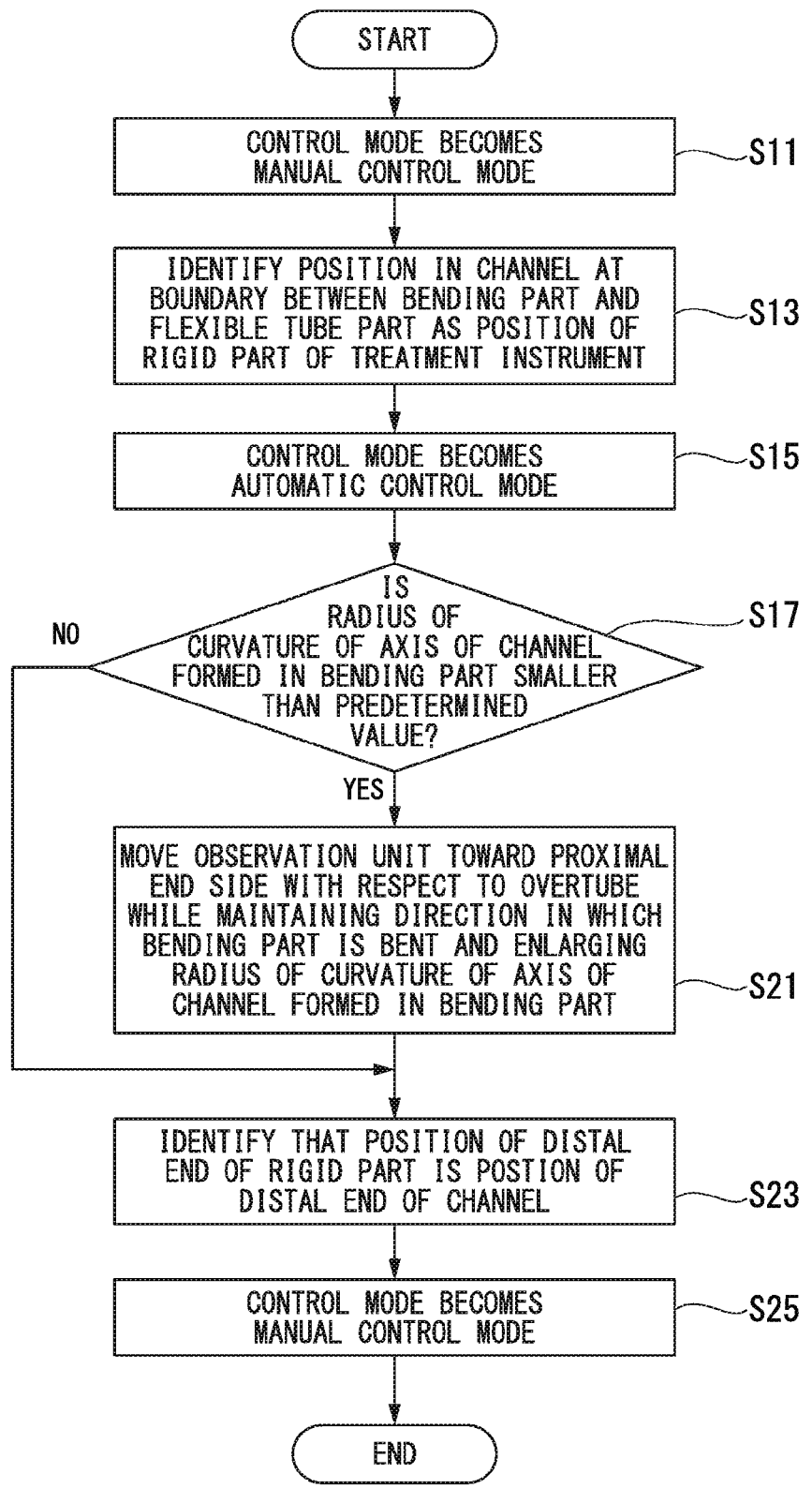
FIG. 7 is a flowchart showing an action of the endoscope system.

Next, an action of the endoscope system 1 constituted as described above will be described. Hereinafter, an operation of, for example, treating a mucous membrane in a body cavity using the endoscope system 1 will be described. FIG. 7 is a flowchart showing an action of the endoscope system 1 of this embodiment.

When the endoscope system 1 is started by operating a switch (not shown), for example, power is supplied from a power source (not shown) to the observation unit 17, the control unit 4, a light source, and so on.

At this time, the control mode of the control part 82 becomes the manual operation mode (step S11).

Illumination light emitted by the light source is supplied to a light guide, and the illumination light guided to the light guide is illuminated to the front of the insertion part 10.

The observation unit 17 acquires an image focused at the light-receiving surface 17a, converts the acquired image into a signal, and transmits the signal to a monitor through the operation part 40. The transmitted signal is converted into the image and displayed on the monitor.

The operator introduces the insertion part 10 and the overtube 3 from a mouth, for example, into a body cavity of a patient while observing the image acquired by the observation unit 17 through the monitor.

The operator introduces the insertion part 10 and the overtube 3 by operating the angular knob 48 as needed. At this time, the bending part 14 is bent to the first side X1 or the second side X2 with respect to the central line C0.

Figure 8:
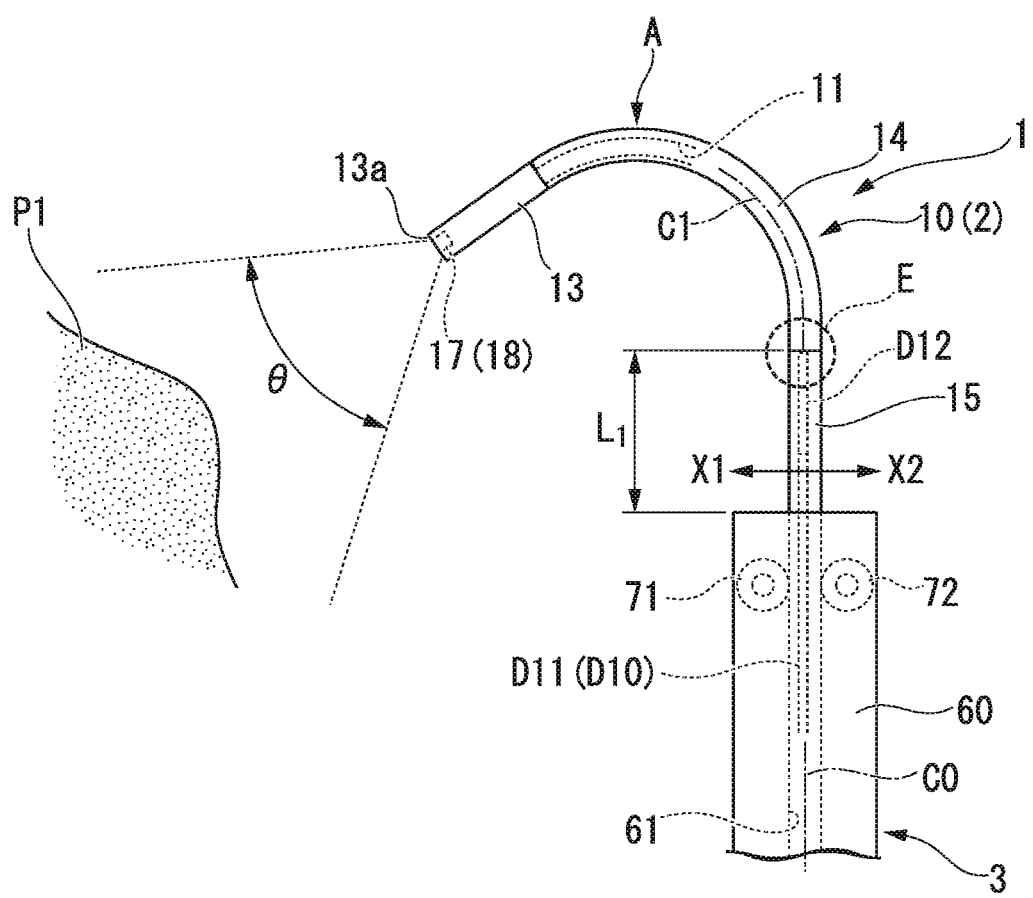
FIG. 8 is a view showing an action of the endoscope system.

As shown in FIG. 8, to cause an object to be treated P1 to be captured within the view, when the bending part 14 is bent to the first side X1 with respect to the central line C0 of the flexible tube part 15, the radius of curvature of the central line C1 of the channel 11 formed in the bending part 14 decreases below the predetermined value described above. That is, to prevent the radius of curvature of the central line C1 of the channel 11 formed in the bending part 14 from decreasing below the predetermined value, the bending part 14 is steeply bent. The bending shape of the bending part 14 in the above case is defined as a bending shape A.

The overtube 3 is pushed into the insertion part 10 up to a state shown in FIG. 8. At this time, by adjusting using scales provided at the insertion part 10, for example, a protruding length L1 of the proximal end of the bending part 14 protruding from the distal end side opening of the insertion part channel 61 is preferably adjusted to be approximately two or three times a retracting length L2 to be described below.

With the switch 49 of the operation part 40, the operator inputs a type of the treatment instrument D10 to be inserted into the channel 11. The computing element of the control part 82 finds a predetermined value which represents the radius of curvature of the central line C1 of the channel 11 formed in the bending part 14 corresponding to the type of the treatment instrument D10 from the table stored in the memory.

The operator grips the operation part main body 41 with one hand and grips the proximal end portion of the treatment instrument D10 with the other hand to insert the distal end rigid part D12 of the treatment instrument D10 into the channel 11 through the forceps hole 47. In addition, for convenience of description, in FIG. 8 and subsequent drawings, the position of the distal end rigid part D12 of the treatment instrument D10 is represented by a dotted circle E.

As shown in FIG. 6, when the distal end rigid part D12 of the treatment instrument D10 passes through the channel 11 and moves forward up to a position of the boundary between the bending part 14 and the flexible tube part 15, the contact 26d and the contact 26c come in contact with each other. The contact information is transmitted to the control part 82 as a signal.

As shown in FIG. 7, in step S13, the control part 82 identifies position information on whether a position of the distal end of the distal end rigid part D12 is at the distal end of the channel 11 formed in the flexible tube part 15, according to a signal transmitted from the proximal end side position sensor 26.

The proximal end side position sensor 26 is disposed at the distal end portion of the channel 11 formed in the flexible tube part 15.

When the control part 82 identified a position in the channel 11 at the boundary between the bending part 14 and the flexible tube part 15 as the position of the distal end rigid part D12 of the treatment instrument D10, steps S13 to S15 are performed. In addition, the proximal end side position sensor 26 is preferably disposed at the distal end portion of the channel 11 formed in the flexible tube part 15, but since the proximal end side position sensor 26 may also be at any position on the channel 11 formed in the flexible tube part 15, the position is not particularly limited thereto.

In step S15, the control part 82 switches the control mode from the manual operation mode to the automatic operation mode and the process proceeds to step S17.

In step S17, the control part 82 determines whether the radius of curvature of the central line C1 of the channel 11 formed in the bending part 14 is smaller than the predetermined value. In this case, the control part 82 determines that the radius of curvature of the central line C1 of the channel 11 formed in the bending part 14 computed by the bending computation device 81 is smaller than the predetermined value (YES in step S17) and the process proceeds to step S21.

Figure 9:
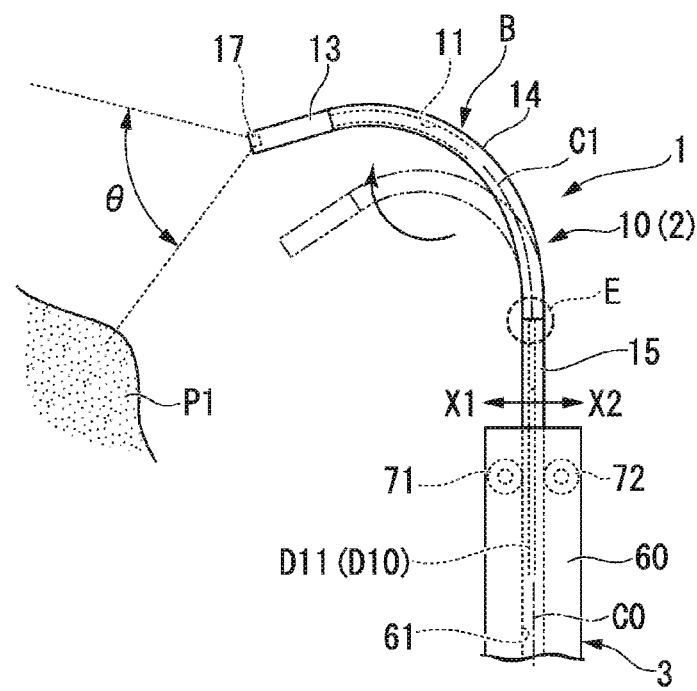
FIG. 9 is a view showing an action of the endoscope system.

In step S21, the control part 82 controls the wire driving motors 42 and 43 to operate the bending part 14 to be bent together with the channel 11 formed in the bending part 14 in a direction in which at least a part of the radius of curvature of the bending part 14 enlarges while maintaining a state in which the bending part 14 is bent to the first side X1 with respect to the central line C0 of the flexible tube part 15 as shown in FIG. 9. In this way, the bending part 14 is bent until the radius of curvature of the central line C1 of the channel 11 formed in the bending part 14 becomes the predetermined value or larger. In addition, the bending shape A of the insertion part 10 in FIG. 8 is shown in FIG. 9 with two-dot chain lines.

Specifically, in the state shown in FIG. 8, by the first operation wire 28a being restored from the neutral position of the bending part 14, the bending part 14 is steeply bent and the bending shape A is formed. Consequently, the control part 82 restores the second operation wire 29a with the second wire operation motor 43 to an extent at which the bending part 14 does not reach the neutral position. In this way, the bending of the bending part 14 to the first side X1 is made gentle (the radius of curvature of the central line C1 of the channel 11 formed in the bending part 14 is enlarged), and a bending shape B of the insertion part 10 shown in FIG. 9 is formed.

Here, by only making the bending of the bending part 14 to the first side X1 gentle, since the bending part 14 comes close to a straight shape, the object to be treated P1 may deviate from the viewing angle θ.

Figure 10:
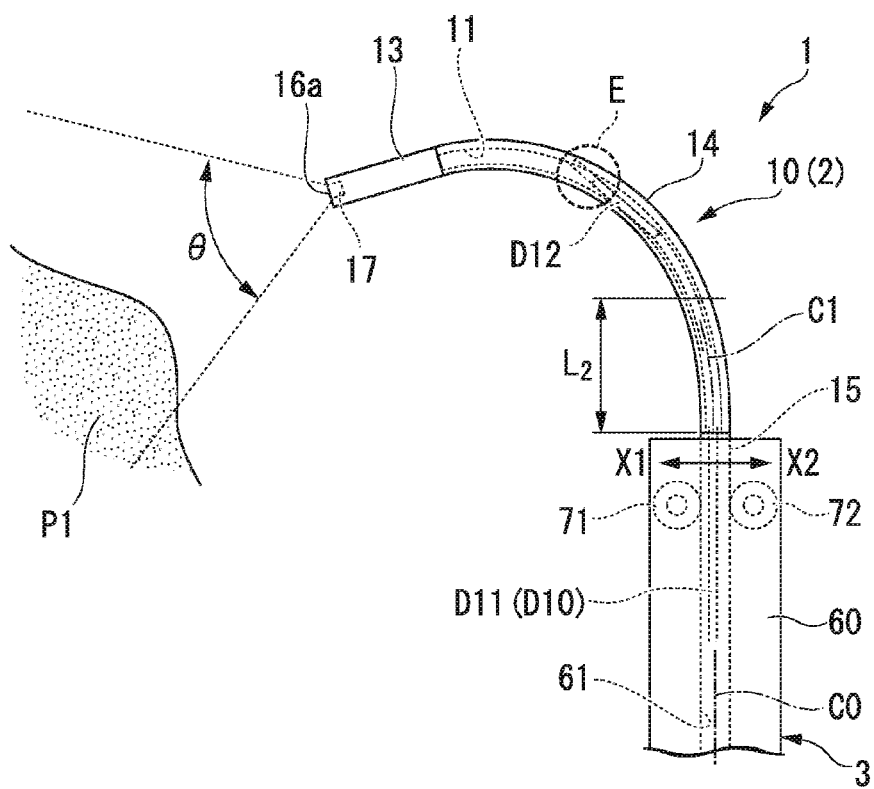
FIG. 10 is a view showing an action of the endoscope system.

Consequently, while the bending of the bending part 14 to the first side X1 is made gentle (along with the bending being made gentle), as shown in FIG. 10, the control part 82 moves the flexible tube part 15 of the insertion part 10 with the first roller driving motor 73 and the second roller driving motor 74 by the retracting length L2 toward the proximal end side with respect to the tube main body 60. That is, the observation unit 17 is moved by the retracting length L2 toward the proximal end side. In this way, the field of view of the observation unit 17 moves toward the object to be treated P1. It becomes easier for the distal end rigid part D12 of the treatment instrument D10 to be inserted into the channel 11 formed in the bending part 14 while limiting the object to be treated P1 from deviating from the view of the observation unit 17. Here, the bending part 14 is prevented from entering the insertion part channel 61.

Operations described above will be described below in detail.

When the distal end rigid part D12 of the treatment instrument D10 reaches the boundary between the flexible tube part 15 and the bending part 14, the position of the distal end rigid part D12 of the treatment instrument D10 is detected by the proximal end side position sensor 26, and the detected result is transmitted from the proximal end side position sensor 26 to the control part 82 as an input signal. When the bending computation device 81 receives the input signal, the bending computation device 81 computes the radius of curvature of the central line of the channel 11, and the control part 82 generates the first driving signal according to the computed result.

In addition, in the memory of the control part 82, a table showing a relation between the radius of curvature of the central line of the channel 11 and the first driving signal is stored. In addition, in the memory, since a table showing a relation between the first driving signal and the retracting length L2 is stored, the retracting length L2 is computed according to the first driving signal, and according to the computed result, the second driving signal which drives the first roller driving motor 73 and the second roller driving motor 74 is generated. In addition, the control part 82 performs control of transmitting the first driving signal to the first wire driving motor 42 and the second wire driving motor 43 and transmitting the second driving signal to the first roller driving motor 73 and the second roller driving motor 74.

In this way, the bending part 14 may be bent in the direction in which the radius of curvature of the central line of the channel 11 enlarges, and the insertion part 10 may be moved back by the retracting length L2 with respect to the overtube 3.

In addition, each of the tables is set in a way that the radius of curvature of the central line of the channel 11 and the retracting length L2 are in balance so that the object to be treated P1 is captured within the view.

With this control, misalignment of the view when the treatment instrument D10 is being inserted into the channel 11 may be prevented.

Figure 11:
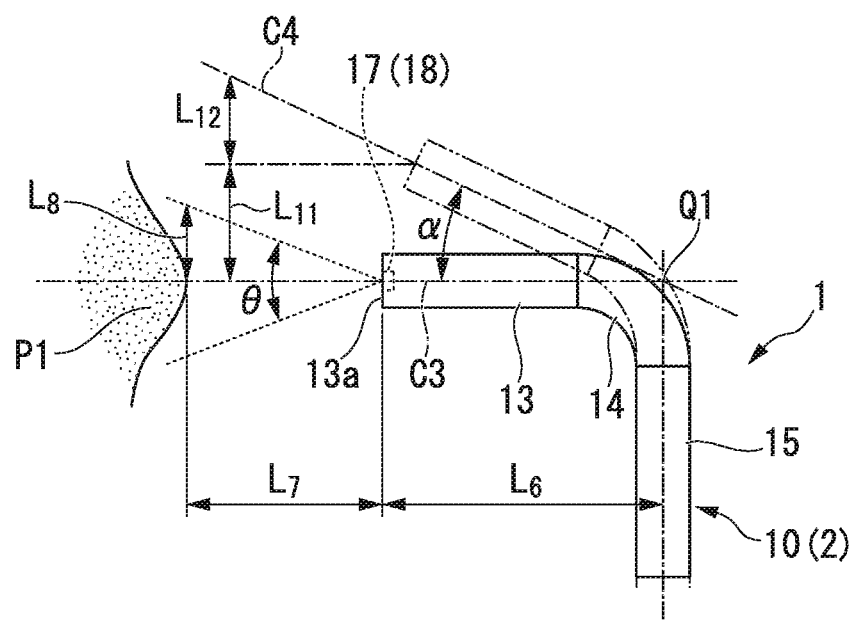
FIG. 11 is a view showing an action of the endoscope system.

Here, with respect to the retracting length L2, a case in which the bending part 14 of the insertion part 10 is formed in a particular shape that is bent at a central angle of approximately 90° as shown in FIG. 11 will be described. In addition, in the following equations, the bending part 14 is formed in the particular shape shown in FIG. 11.

A known means for measuring a distance from the distal end surface 13a of the insertion part 10 to the object to be treated may be used as the distance measurement part 18. As the distance measurement part 18, for example, a time-of-flight (TOF) type distance sensor which measures a distance up to an object to be treated according to the time laser beams are radiated until they are reflected back by the object to be treated and detected may be used. Here, a configuration of the distance measurement part 18 is not limited thereto.

In addition, in the memory of the control part 82, a value of the viewing angle θ of the observation unit 17, longitudinal lengths of the rigid part 13 and the bending part 14, for example, are stored.

In addition, in the memory, a table showing a correlation between the radius of curvature of the axis C1 of the channel 11 formed in the bending part 14 and a position of an optical axis C3 (refer to FIG. 11) with respect to the proximal end of the bending part 14 is stored.

An intersection point between the optical axis C3 of the observation unit 17 before the bending of the bending part 14 is made gentle and an optical axis C4 of the observation unit 17 after the bending of the bending part 14 is made gentle is a point Q1. In addition, in FIG. 11, the shape of the insertion part 10 after the bending of the bending part 14 is made gentle is shown with two-dot chain lines.

The length along the optical axis C3 from the point Q1 to the distal end surface 13a of the insertion part 10 is defined as L6. An angle formed between the optical axis C3 and the optical axis C4 is defined as α. The distance from the distal end surface 13a of the insertion part 10 to the object to be treated P1 before the bending of the bending part 14 is made gentle is defined as L7. The distance L7 is measured by the distance measurement part 18. A distance L8 from the center of view to a limit of view is obtained using the viewing angle θ and the distance L7 as in Equation (1), for example.

$$L8 = L7 \times \tan(\theta/2) \quad (1)$$

A movement amount L11 (in a direction perpendicular to the optical axis C3) of the position of the distal end surface 13a of the insertion part 10 when the bending of the bending part 14 is made gentle is obtained from Equation (2).

$$L11 = L6 \times \sin(\alpha) \quad (2)$$

A movement amount L12 of the center of view due to the optical axis C4 of the observation unit 17 being tilted by the angle α with respect to the optical axis C3 is obtained from Equation (3).

$$L12 = L7 \times \tan(\alpha) \quad (3)$$

When the flexible tube part 15 of the insertion part 10 is moved toward the proximal end side by the retracting length L2 while the bending of the bending part 14 is made gentle, a condition that the object to be treated P1 be within the field of view is obtained from Equation (4).

$$L2 - (L11 + L12) < L8 \quad (4)$$

Equation (1) to Equation (3) are substituted into Equation (4) to obtain Equation (5).

$$L2 - \{L6 \times \sin(\alpha) + L7 \times \tan(\alpha)\} < L7 \times \tan(\theta/2) \quad (5)$$

Since the retracting length L2 is a value which is 0 or greater, Equation (5) is combined with a modified equation to obtain Equation (6).

$$0 \le L2 < \{L6 \times \sin(\alpha) + L7 \times \tan(\alpha)\} + L7 \times \tan(\theta/2) \quad (6)$$

When the retracting length L2 is set to satisfy Equation (6), the object to be treated P1 is within the field of view (viewing angle θ) of the observation unit 17.

Figure 12:
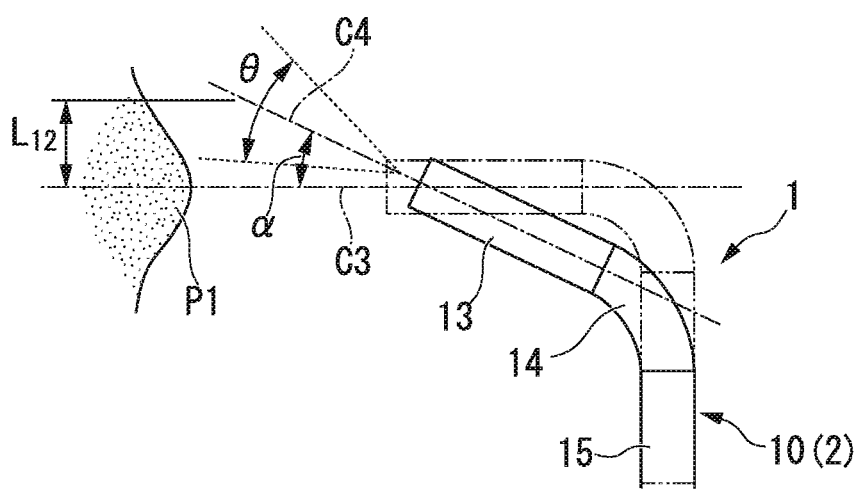
FIG. 12 is a view showing an action of the endoscope system.

When the retracting length L2 is the movement amount L11, as shown in FIG. 12, the center of view is misaligned by the movement amount L12 before and after the bending of the bending part 14 is made gentle. In addition, in FIGS. 12 and 13, the shape of the insertion part 10 before the bending of the bending part 14 is made gentle is shown with two-dot chain lines.

Figure 13:
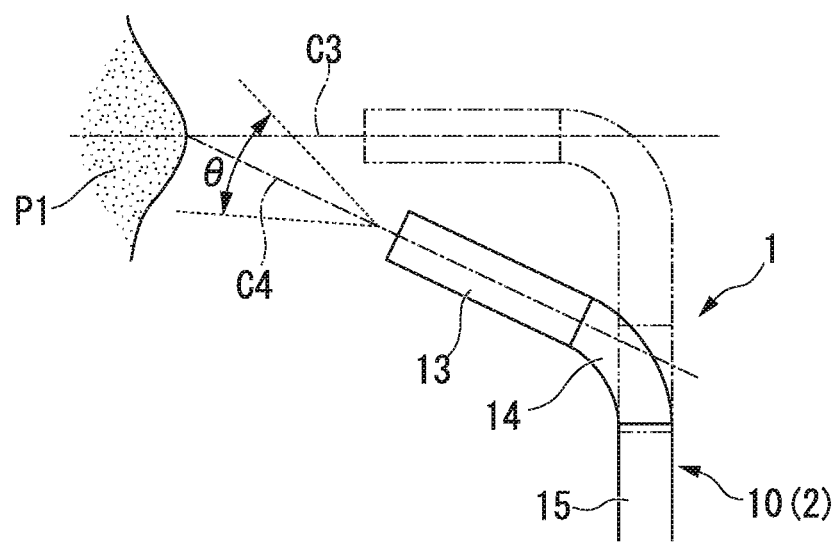
FIG. 13 is a view showing an action of the endoscope system.

Meanwhile, when the retracting length L2 is the sum of the movement amount L11 and the movement amount L12, as shown in FIG. 13, the center view is aligned before and after the bending of the bending part 14 is made gentle.

After the process, the process of the control part 82 proceeds to step S23.

In step S17, whether the radius of curvature of the central line C1 of the channel 11 formed in the bending part 14 is the predetermined value or greater is detected by the bending computation device 81, and when the control part 82 determines NO, the process proceeds to step S23.

When the operator pushes the treatment instrument D10 further into the channel 11, the distal end rigid part D12 of the treatment instrument D10 is inserted into the channel 11 formed in the bending part 14.

In step S23, the control part 82 identifies position information on whether the position of the distal end of the distal end rigid part D12 is in the opening 11a (distal end) of the channel 11 according to a signal transmitted from the distal end side position sensor 27.

When the control part 82 identifies that the distal end rigid part D12 of the treatment instrument D10 is in the opening 11*a* of the channel 11, the process of the control part 82 proceeds to step S25 from step S23.

At this time, the distal end rigid part D12 moves further toward the distal end side than the channel 11 formed in the bending part 14 to be disposed in the channel 11 formed in the rigid part 13.

In step S25, the control part 82 switches the control mode from the automatic operation mode to the manual operation mode. When the operator pushes the treatment instrument D10 further, the distal end rigid part D12 of the treatment instrument D10 protrudes further toward the distal end side than the opening 11*a* of the channel 11.

In the manual operation mode, the operator operates the angular knob 48 as needed to bend the bending part 14. The operator may grip the object to be treated P1 at the distal end rigid part D12 protruding further toward the distal end side than the opening 11*a*.

As described above, according to the endoscope system 1 of this embodiment, when the operator has inserted the treatment instrument D10 into the channel 11 of the endoscope apparatus 2, and the proximal end side position sensor 26 has detected the position of the distal end of the distal end rigid part D12 in the channel 11 formed in the flexible tube part 15, the following process is performed. That is, when it is detected that the radius of curvature of the central line C1 of the channel 11 formed in the bending part 14 is smaller than the predetermined value and the direction in which the bending part 14 is bent is the first side X1 with respect to the central line C0 of the flexible tube part 15, the bending part 14 is bent so that the radius of curvature of the central line C1 of the channel 11 formed in the bending part 14 becomes the predetermined value or larger while the state in which the bending part 14 is bent to the first side X1 with respect to the central line C0 of the flexible tube part 15 is maintained. Along with this, the flexible tube part 15 of the insertion part 10 is moved toward the proximal end side by the first roller driving motor 73 and the second roller driving motor 74.

When the bending of the bending part 14 is made gentle, since the bending part 14 comes close to a straight shape, the view of the observation unit 17 deviates from the object to be treated P1. However, by moving the field of view of the observation unit 17 toward the object to be treated P1 by moving the insertion part 10 toward the proximal end side, the treatment instrument D10 at which the distal end rigid part D12 is provided may be easily inserted into the channel 11 while the view of the observation unit 17 is limited from deviating from the object to be treated P1.

The movement mechanism 70 includes the pair of rollers 71 and 72 and the roller driving motors 73 and 74. In this way, the movement mechanism 70 may be simply constituted.

In addition, in the embodiment, the radius of curvature of the central line C1 of the channel 11 formed in the bending part 14 may also be detected by the following method.

For example, a potentiometer may be provided at the rigid part 13 or the joint rings 21 and 22, and a swiveling angle of the rigid part 13 or the joint rings 21 and 22 may be detected.

The radius of curvature of the central line C1 of the channel 11 formed in the bending part 14 may also be detected by providing an attitude sensor at each of the distal end and the proximal end of the channel 11 formed in the bending part 14.

When the operation wires 28*a* and 29*a* are being restored, tensions of the operation wires 28*a* and 29*a* may be detected by, for example, a load cell, and the radius of curvature of the central line C1 of the channel 11 formed in the bending part 14 may be obtained.

The position of the distal end of the distal end rigid part D12 of the treatment instrument D10 being the position of the distal end of the channel 11 formed in the flexible tube part 15 may also be detected as below.

Figure 14:
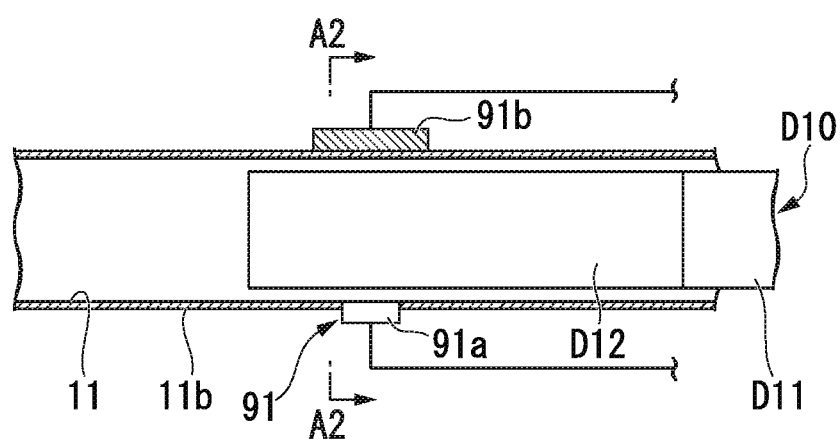
FIG. 14 is a cross-sectional view of a lateral surface showing a proximal end side position sensor of an endoscope system according to a modified example of the first embodiment of the present invention.
Figure 15:
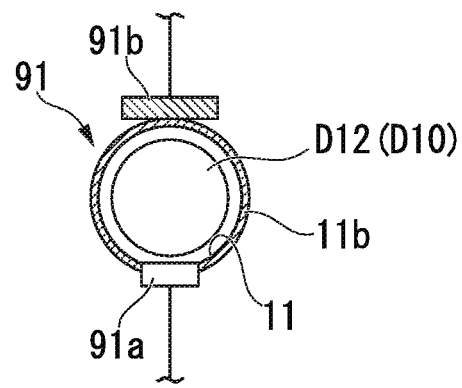
FIG. 15 is a cross-sectional view taken along section line A2-A2 in FIG. 14.

In a modified embodiment shown in FIGS. 14 and 15, a proximal end side position sensor 91 includes a light-emitting part 91*a* which emits light such as visible light and a light-receiving part 91*b* which detects the light emitted by the light-emitting part 91*a*. The light-emitting part 91*a* and the light-receiving part 91*b* are disposed to face each other at the distal end of the channel 11 formed in the flexible tube part 15. The light-emitting part 91*a* continuously emits light toward the light-receiving part 91*b*. Due to the distal end of the distal end rigid part D12 of the treatment instrument D10 being inserted between the light-emitting part 91*a* and the light-receiving part 91*b*, the light-receiving part 91*b* becomes unable to detect light emitted by the light-emitting part 91*a* that was being detected before.

Figure 16:
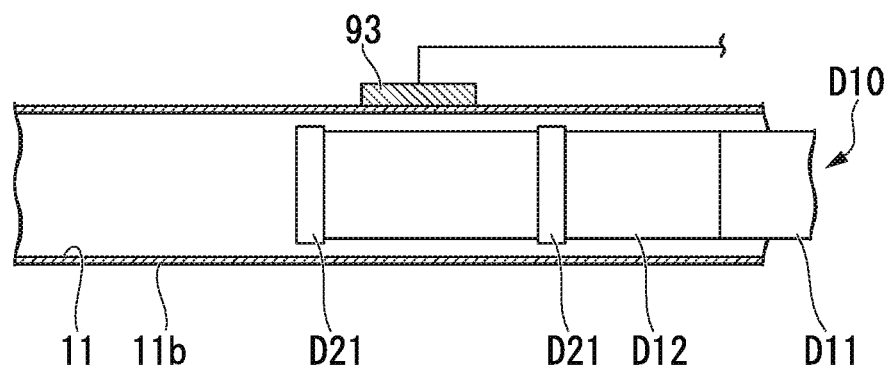
FIG. 16 is a cross-sectional view of a lateral surface showing the proximal end side position sensor of the endoscope system according to the modified example of the first embodiment of the present invention.

In a modified embodiment shown in FIG. 16, a proximal end side position sensor 93 may have a Hall sensor, and ring-shaped permanent magnets D21 may be provided at outer circumferential surfaces of the distal end and the proximal end, respectively, of the distal end rigid part D12 of the treatment instrument D10. When the permanent magnet D21 provided at the distal end of the distal end rigid part D12 comes closer to the proximal end side position sensor 93, the Hall sensor detects a change in a magnetic field.

Figure 17:
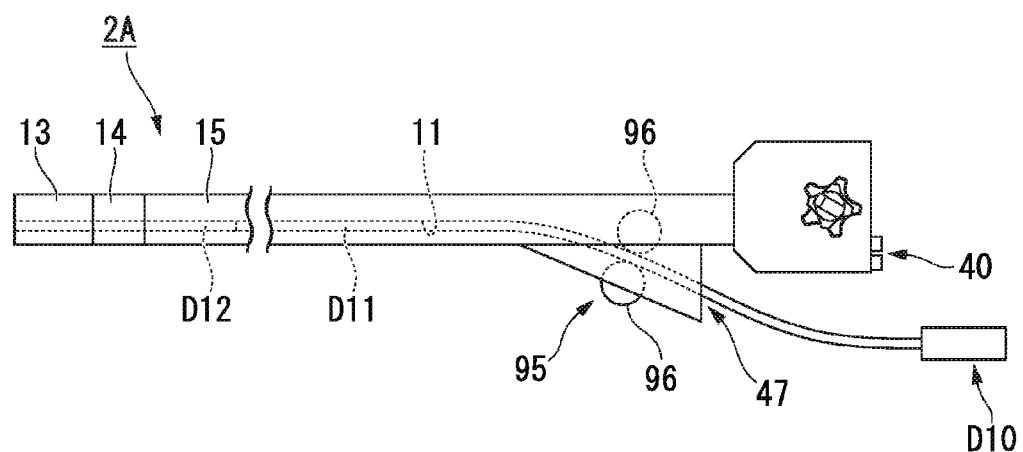
FIG. 17 is a view schematically showing a modified example of the endoscope apparatus according to the first embodiment of the present invention.

From a length of the treatment instrument insertion part D11 of the treatment instrument D10 inserted into the channel 11, a proximal end side position sensor 95 of an endoscope apparatus 2A shown in FIG. 17 detects that the position of the distal end of the distal end rigid part D12 of the treatment instrument D10 is the position of the distal end of the channel 11 formed in the flexible tube part 15.

The proximal end side position sensor 95 includes a pair of rollers 96 provided in such a way that portions thereof protrude from an inner circumferential surface of the proximal end portion of the channel 11 and a computing element or memory (not shown), and so on.

The pair of rollers 96 rotate according to the length of the treatment instrument insertion part D11 inserted into the channel 11. In the memory, a length from the pair of rollers 96 to the distal end of the channel 11 formed in the flexible tube part 15 in a longitudinal direction of the channel 11, for example, is stored.

From a number of rotations of the rollers 96, the computing element calculates the length of the treatment instrument insertion part D11 of the treatment instrument D10 inserted further toward the distal end side than the pair of rollers 96 in the channel 11. In addition, by comparing the calculated length to the length stored in the memory, it is detected that the position of the distal end of the distal end rigid part D12 of the treatment instrument D10 is the position of the distal end of the channel 11 formed in the flexible tube part 15.

In the modified embodiment, the position of the distal end of the distal end rigid part D12 of the treatment instrument D10 may be detected both times when the treatment instrument D10 is being inserted into the channel 11 and when the treatment instrument D10 is being extracted from the channel 11.

In addition, in this embodiment, after treating with the treatment instrument D10 is finished, there are cases in which the treatment instrument D10 is replaced with another treatment instrument while the insertion part 10 and the overtube 3 of the endoscope apparatus 2 are introduced into a body cavity.

At this time, before the treatment instrument D10 is restored, the radius of curvature of the central line C1 of the channel 11 formed in the bending part 14 is a predetermined value or greater. The treatment instrument D10 is extracted from the channel 11. When the operator inserts another treatment instrument into the channel 11 and the bending part 14 is steeply bent, the control part 82 makes the bending of the bending part 14 gentle while moving the flexible tube part 15 of the insertion part 10 by the retracting length L2 as described above.

In this manner, even when the treatment instrument is being replaced, due to the protruding length L1 described above being twice the retracting length L2 or more, the flexible tube part 15 of the insertion part 10 may be moved toward the proximal end side twice or more by the first roller driving motor 73 and the second roller driving motor 74.

In addition, in this modified embodiment, when the endoscope system 1 detects that the treatment instrument D10 is extracted from the channel 11, the endoscope system 1 may be configured in such a way that the overtube 3 automatically moves the flexible tube part 15 of the insertion part 10 toward the distal end side by the retracting length L2 when the insertion part 10 is being moved toward the proximal end side by the retracting length L2.

In this way, even when the treatment instrument is replaced several times, the treatment instrument at which the rigid part is provided may be easily inserted into the channel 11 while the view of the observation unit is limited from deviating from the object to be treated P1. In this case, the first roller driving motor 73 and the second roller driving motor 74 become constitutions (reciprocating mechanisms) which may move the flexible tube part 15 toward the proximal end side as well as the distal end side.

In addition, in this embodiment, a table showing a correlation between the rotational amounts of the rotational shafts of the wire driving motors 42 and 43 from the reference positions and the radius of curvature of the central line C1 of the channel 11 formed in the bending part 14 when the bending part 14 is bent is not stored in the memory of the bending computation device 81, and the control part performs image processing to be described below.

The control part calculates an amount of misalignment and a vector between an image when the object to be treated P1 is captured and an image when the field of view of the observation unit is misaligned with respect to the object to be treated P1. In addition, the rotational amounts of the rollers 71 and 72 are calculated according to the amount of misalignment and the vector.

Second Embodiment

Next, a second embodiment of the present invention will be described with reference to FIGS. 18 to 24. However, like reference numerals will be given to parts overlapping with the embodiment above, descriptions thereof will be omitted, and only differences from the embodiment above will be described.

As shown in FIG. 18, an endoscope system 6 of this embodiment includes a soft insertion part 100 at which the channel 11 is formed, an operation part 150 provided at a proximal end portion of the insertion part 100, and a control unit 160 which controls the operation part 150.

The insertion part 100 has a constitution in which an expansion-and-contraction mechanism (moving part, expansion-and-contraction part) 130 is provided at a longitudinal middle portion of the flexible tube part 15 of the insertion part 10 of the first embodiment.

Figure 19:
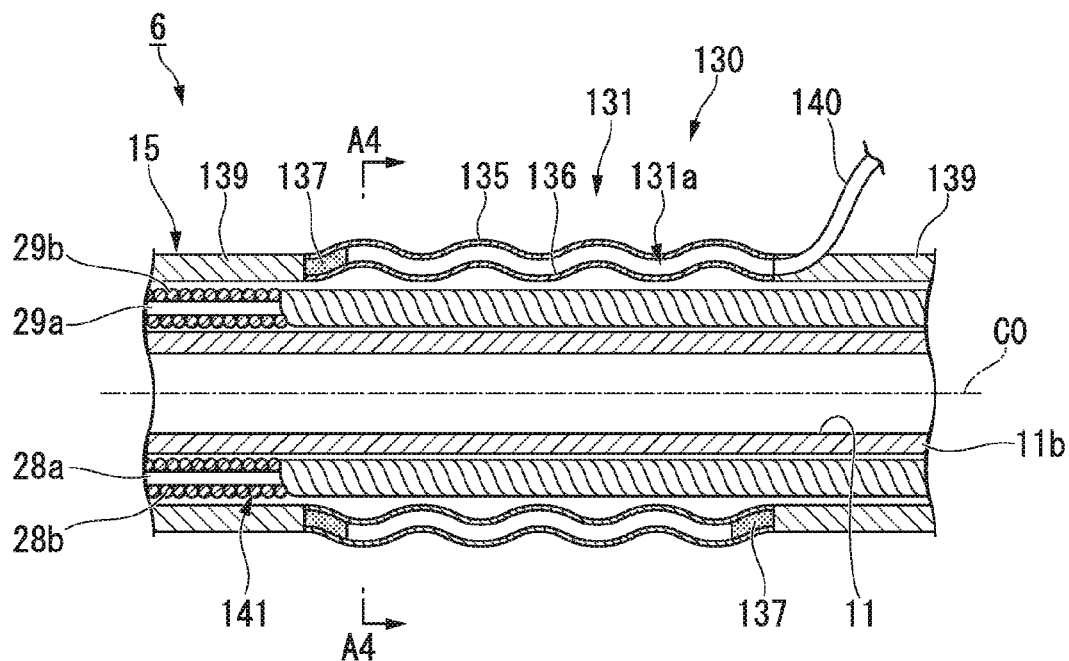
FIG. 19 is a cross-sectional view of a lateral surface of a flexible tube part of the endoscope system.
Figure 20:
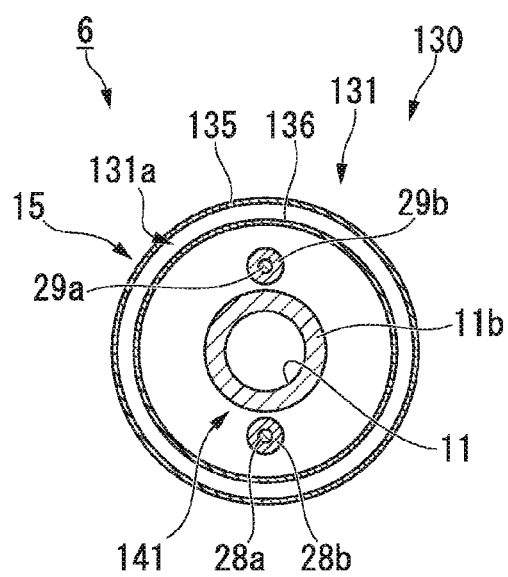
FIG. 20 is a cross-sectional view taken along section line A4-A4 in FIG. 19.
Figure 21:
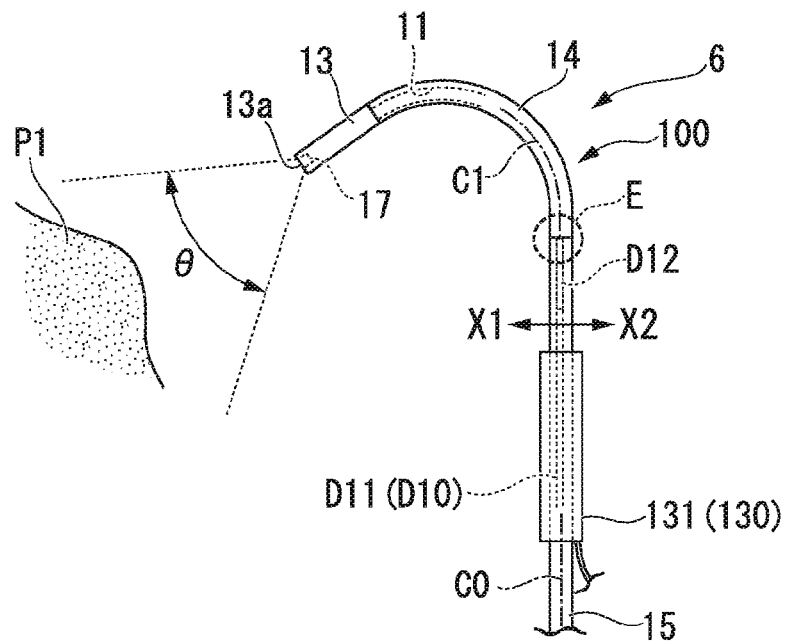
FIG. 21 is a view showing an action of the endoscope system.

As shown in FIGS. 18 to 20, the expansion-and-contraction mechanism 130 includes a bellows part 131 and a fluid control part 132 which supplies a fluid to a sealed space 131a formed in the bellows part 131 or suctions the fluid in from the sealed space 131a.

The bellows part 131 includes an outer wall 135 and an inner wall 136 formed with a soft material such as polypropylene, and sealing members 137 which respectively seal distal end portions and proximal end portions of the outer wall 135 and the inner wall 136. The sealing space 131a is formed by the outer wall 135, the inner wall 136, and the sealing members 137.

All of the distal end portion and the proximal end portion of the outer wall 135 and the distal end portion and the proximal end portion of the inner wall 136 are connected to an outer tube 139 that constitutes an outer surface of the flexible tube part 15. The outer tube 139 is formed to have flexibility and somewhat high bending stiffness in order to maintain its shape even if it is a single body.

A distal end portion of a fluid supply tube 140 is connected to the proximal end portion of the bellows part 131. The fluid control part 132 is connected to a proximal end portion of the fluid supply tube 140.

In addition, the bellows part 131 in FIGS. 18 to 20 is extended along the central line C0 of the flexible tube part 15 due to a fluid being supplied to the sealing space 131a.

As shown in FIGS. 19 and 20, the tube 11b which forms the channel 11, the operation wires 28a and 29a, the coil sheaths 28b and 29b described above, and a light guide (not shown) or signal lines (hereinafter, these will be collectively referred to as a linear body 141) are inserted into the outer tube 139 and the bellows part 131. The linear body 141 is preferably tied with a band member, for example, at a few places in the direction of the central line C0.

The linear body 141 is connected to the bending part 14, for example, further toward the distal end side than the bellows part 131.

As shown in FIG. 18, the operation part 150 includes a distal end side operation part 151 provided at the proximal end portion of the insertion part 100 and a proximal end side operation part 152 provided apart from the distal end side operation part 151.

The proximal end portion of the outer tube 139 is mounted on an operation part main body 151a of the distal end side operation part 151. The angular knob 48 described above is provided at the proximal end side of the operation part main body 151a.

A storage part 156 is connected to the operation part main body 151a via a distal end side universal cord 155. The storage part 156 and an operation part main body 152a of the proximal end side operation part 152 are connected via a proximal end side universal cord 157.

The wire driving motors 42 and 43 described above are disposed in the operation part main body 152a.

The linear body 141 extended further toward the proximal side than the outer tube 139 in the operation part main body 151a is inserted into the operation part main body 151a and the distal end side universal cord 155 and is stored in a state in which it is bent by a predetermined length in the storage part 156. The linear body 141 is inserted into the storage part 156 and the proximal end side universal cord 157 and is extended up to the operation part main body 152a.

The proximal end portions of the operation wires 28a and 29a that constitute the linear body 141 are connected to the wire driving motors 42 and 43.

In the tube 11b which constitutes the linear body 141 of a part disposed in the storage part 156, a through-hole 11f is formed. In the storage part 156, a through-hole 156a is formed. The treatment instrument D10 is inserted into the channel 11 through the through-hole 156a of the storage part 156 and the through-hole 11f of the tube 11b.

The control unit 160 includes the bending computation device 81 described above and a control part 161.

The control part 161 performs controlling of the wire driving motors 42 and 43 or the fluid control part 132.

Next, an action of the endoscope system 6 constituted in this way will be described.

The operator introduces the insertion part 100 into a body cavity of a patient and causes the distal end surface 13a of the insertion part 100 to face the object to be treated P1 so that the object to be treated P1 is within the viewing angle θ.

When it is determined that the distal end of the distal end rigid part D12 has reached the distal end of the channel 11 formed in the flexible tube part 15, the radius of curvature of the central line C1 of the channel 11 formed in the bending part 14 is smaller than a predetermined value, or the direction in which the bending part 14 is bent is the first side X1 with respect to the central line C0, the control part 161 performs a process below.

Figure 22:
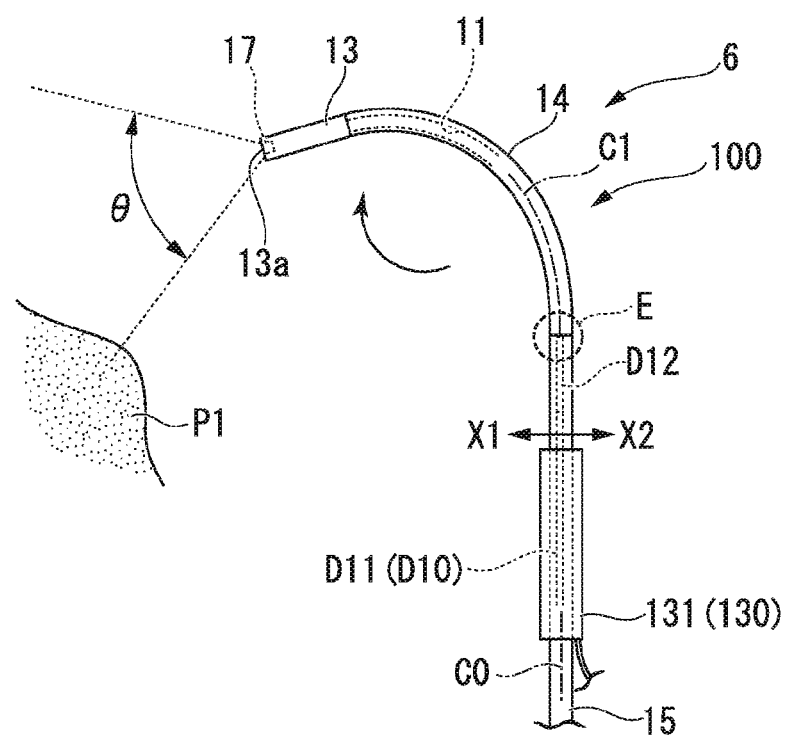
FIG. 22 is a view showing an action of the endoscope system.

That is, as shown in FIG. 22, the bending part 14 is bent so that the radius of curvature of the central line C1 of the channel 11 formed in the bending part 14 is a predetermined value or larger while the state in which the bending part 14 is bent to the first side X1 with respect to the central line C0 is maintained. Here, by only making the bending of the bending part 14 to the first side X1 gentle, since the bending part 14 comes close to a straight shape, the object to be treated P1 may deviate from the viewing angle θ of the observation unit 17.

Figure 23:
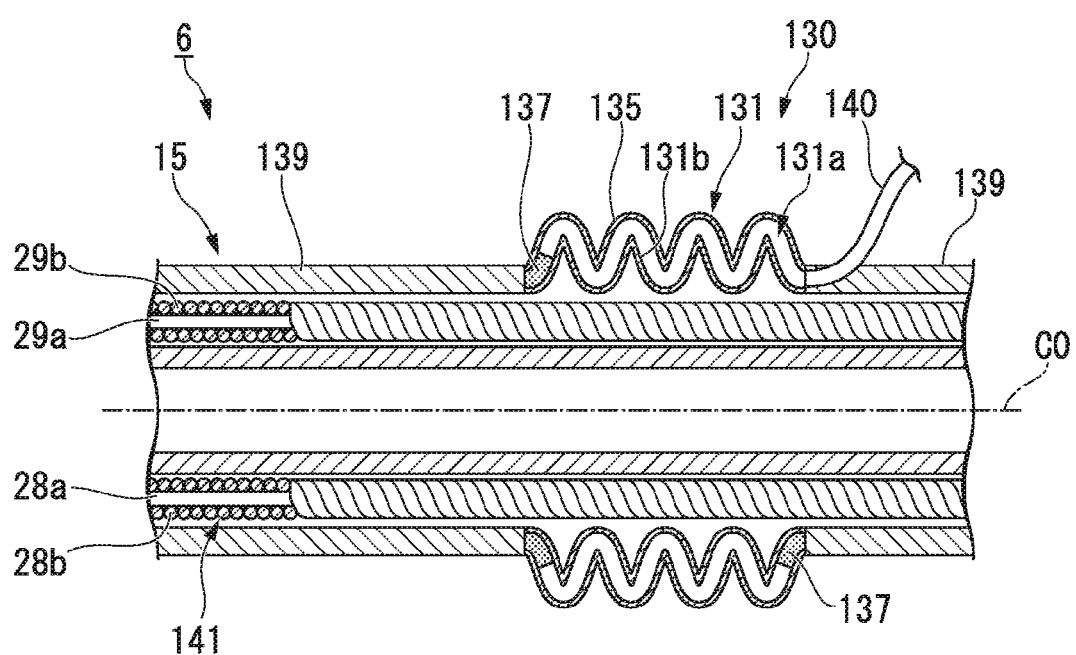
FIG. 23 is a cross-sectional view showing an action of the endoscope system.
Figure 24:
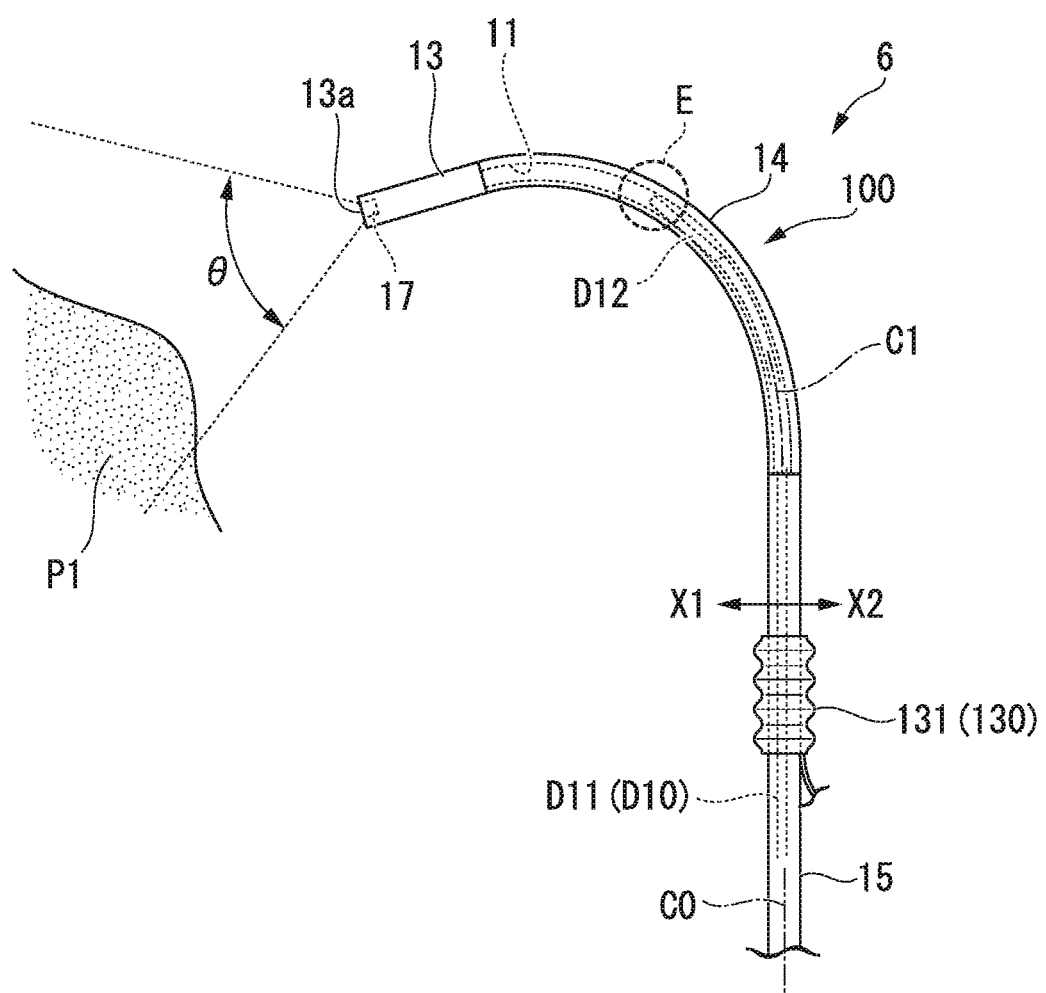
FIG. 24 is a view showing an action of the endoscope system.

Consequently, the control part 161 makes the bending of the bending part 14 to the first side X1 to be gentle, causes the fluid in the sealing space 131a to be suctioned by the fluid control part 132 and, as shown in FIGS. 23 and 24, and causes the bellows part 131 to be contracted in the direction of the central line C0.

Since the linear body 141 is connected to the bending part 14, for example, further toward the distal end side than the bellows part 131, the bending part 14 moves toward the proximal end side together with the outer tube 139 which is further toward the distal end side than the bellows part 131. The linear body 141 inserted into the operation part main body 151a and the distal end side universal cord 155 moves toward the proximal end side, and thus the length of the linear body 141 bent in the storage part 156 becomes longer.

As described above, according to the endoscope system 6 of this embodiment, even when the bending part 14 is bent, the treatment instrument D10 may be easily inserted into the channel 11 while the view of the observation unit 17 is limited from deviating from the object to be treated P1.

Although the first embodiment and the second embodiment of the present invention have been described in detail above with reference to the drawings, specific constitutions are not limited to the embodiments above and also include modifications, combinations, deletions, and so on, of constitutions within the scope not departing from the gist of the present invention. In addition, of course each of the constitutions shown in each of the embodiments may be used in proper combinations.

In addition, the present invention is not limited to the descriptions above and is limited only by the scope of the attached claims.

For example, according to the first embodiment and the second embodiment, the manual operation mode and the automatic operation mode of the control mode are automatically switched according to the position of the distal end rigid part D12 in the channel 11. However, the manual operation mode and the automatic operation mode may also be configured to be switched manually when the operator operates the switch, for example, of the operation part.

In addition, the distal end side position sensor 27 may not be included. This is because the control mode may also be manually switched to the manual operation mode after checking, from the position of the distal end rigid part D12 in the channel 11 when the control mode is switched from the manual operation mode to the automatic operation mode, that the treatment instrument D10 is further pushed in as much as the length of the channel 11 formed in the bending part 14 and the length of the distal end rigid part D12.

Although the observation part has been described as having the imaging element in the first embodiment and the second embodiment, the observation part may be an image guide. In this case, the distal end surface which is a light-receiving surface of the image guide is provided further toward the distal end side than the bending part 14 of the insertion part 10.

Although the distal end rigid part D12 has been described as being provided at the distal end portion in the longitudinal direction of the treatment instrument D10, the rigid part may also be provided at a middle portion in the longitudinal direction of the treatment instrument.

The invention claimed is:

1. An endoscope system comprising:
  an insertion part having flexibility, a flexible tube part, a bending part, and an instrument channel into which a medical instrument is insertable formed therein;
  the flexible tube part provided at a proximal end portion of the insertion part;
  the bending part provided at a distal end portion of the insertion part and bendable with respect to a distal end portion of the flexible tube part;
  a tubular body in which an insertion part channel into which the flexible tube part is insertable is formed and provided to be movable along a longitudinal axis of the flexible tube part with respect to the flexible tube part;
  a first driving part configured to operate the bending part to be bent with respect to the distal end portion of the flexible tube part;
  a second driving part provided at the tubular body to move the flexible tube part inserted into the insertion part channel with respect to the tubular body;
  a processor comprising hardware; a connection part that connects the flexible tube part and the bending part; and
  a sensor, the sensor configured to detect a position of a distal end rigid part of the medical instrument which moves within the instrument channel and to transmit a result of detecting the position of the distal end rigid part of the medical instrument as an input signal to the processor, the processor configured to
  control the first driving part so that the bending part bends in a direction in which a radius of curvature of a central axis of the instrument channel enlarges and control the second driving part so that the flexible tube part moves toward a proximal end portion with respect to the tubular body according to the driving amount of the first driving part;

wherein the processor is further configured to compute the radius of curvature of the central axis of the instrument channel when the input signal is received, and control the first driving part according to a result of the processor computing the radius of curvature.

2. The endoscope system according to claim 1, wherein the control part controls the second driving part so that the flexible tube part moves in the longitudinal direction with respect to the tubular body.

3. The endoscope system according to claim 1 further comprising:
an observation unit provided at a distal end of the bending part, wherein:
the processor is configured to control the second driving part so that the field of view of the observation unit after the bending part is operated to be bent includes a center of the field of view of the observation unit before the bending part is operated to be bent.

4. An endoscope system comprising:
an insertion part having flexibility, a flexible tube part, a bending part and an instrument channel into which a medical instrument is insertable formed therein;
the flexible tube part provided at a proximal end portion of the insertion part;
the bending part provided at a distal end portion of the insertion part and bendable with respect to a distal end portion of the flexible tube part;
a tubular body in which an insertion part channel into which the flexible tube part is insertable is formed and provided to be movable along a longitudinal axis of the flexible tube part with respect to the flexible tube part;
a first driving part configured to operate the bending part to be bent with respect to the distal end portion of the flexible tube part;
a second driving part provided at a distal end portion of the tubular body to move the flexible tube part inserted into the insertion part channel toward a proximal end portion with respect to the tubular body;
a processor comprising hardware, the processor configured to generate a first driving signal which drives the first driving part so that the bending part is operated to be bent in a direction in which a radius of curvature of a central axis of the instrument channel enlarges and a second driving signal which drives the second driving part according to a first driving signal which drives the first driving part, and configured to perform control for transmitting the first driving signal to the first driving part and transmitting the second driving signal to the second driving part; and
a sensor provided at a connection part configured to connect the flexible tube part to the bending part, the sensor configured to detect a position of a distal end rigid part of the medical instrument which moves within the instrument channel and to transmit a result of detecting the position of the distal end rigid part of the medical instrument as an input signal to the processor,
wherein the processor is further configured to compute the radius of curvature of the central axis of the instrument channel when the input signal is received and, generates the first driving signal according to a result of the processor computing the radius of curvature.

5. The endoscope system according to claim 4, wherein the second driving part moves the flexible tube part in the longitudinal direction with respect to the tubular body according to the second driving signal from the processor.

6. The endoscope system according to claim 4 further comprising:
an observation unit provided at a distal end of the bending part, wherein:
the processor is configured to generate the second driving signal so that the field of view of the observation unit after the bending part is operated to be bent according to the first driving signal includes a center of the field of view of the observation unit before the bending part is operated to be bent.

\* \* \* \* \*